US010548844B2

(12) United States Patent
Anselmo et al.

(10) Patent No.: US 10,548,844 B2
(45) Date of Patent: Feb. 4, 2020

(54) PH-RESPONSIVE MUCOADHESIVE POLYMERIC ENCAPSULATED MICROORGANISMS

(71) Applicant: Massachusetts Institute of Technology, Cambridge, MA (US)

(72) Inventors: Aaron C. Anselmo, Cambridge, MA (US); Robert S. Langer, Newton, MA (US); Ana Jaklenec, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/372,703

(22) Filed: Dec. 8, 2016

(65) Prior Publication Data

US 2017/0165201 A1    Jun. 15, 2017

Related U.S. Application Data

(60) Provisional application No. 62/333,570, filed on May 9, 2016, provisional application No. 62/267,121, filed on Dec. 14, 2015.

(51) Int. Cl.
*A61K 9/16* (2006.01)
*A61K 35/741* (2015.01)
(Continued)

(52) U.S. Cl.
CPC .......... *A61K 9/1652* (2013.01); *A61K 9/1641* (2013.01); *A61K 35/741* (2013.01);
(Continued)

(58) Field of Classification Search
CPC .. A61K 9/1641; A61K 9/5026; A61K 9/5036; A61K 9/5073; A61K 9/5089;
(Continued)

(56) References Cited

U.S. PATENT DOCUMENTS

| 6,368,586 B1 | 4/2002 | Jacob |
| 2003/0109025 A1 | 6/2003 | Durand |

(Continued)

FOREIGN PATENT DOCUMENTS

| WO | 2009070012 | 6/2009 |
| WO | WO 2009/070012 | 6/2009 |

OTHER PUBLICATIONS

Cook et al. "Layer-by-layer coating of alginate matrices with chitosan-alginate fro the improved survival and targeted delivery of probiotic bacteria after oral administration" in the Journal of Materials Chemistry B, 2013, 1, 52-60, published on line on Nov. 5, 2012).*

(Continued)

*Primary Examiner* — Blessing M Fubara
(74) *Attorney, Agent, or Firm* — Pabst Patent Group LLP

(57) ABSTRACT

Methods of encapsulating microorganisms, or components thereof, for targeted enteric delivery to an animal host have been developed. In particular, the encapsulation provides a prolonged survival, extended retention and a pH-sensitive release of the encapsulated microorganisms or antigenic components thereof at targeted sites within the gastrointestinal tract. The formulations are useful for diagnostic, therapeutic and prophylactic purposes and can alter a host's microbial composition associated with a condition or a disease state.

17 Claims, 10 Drawing Sheets

(51) Int. Cl.
  *A61K 35/742* (2015.01)
  *A61K 35/745* (2015.01)
  *A61K 35/747* (2015.01)
(52) U.S. Cl.
  CPC .......... *A61K 35/742* (2013.01); *A61K 35/745* (2013.01); *A61K 35/747* (2013.01)
(58) Field of Classification Search
  CPC .. A61K 9/1652; A61K 35/741; A61K 35/745; A61K 35/747; A61K 35/76; A61K 39/07; A61K 39/12; A61K 36/064; A61K 2039/542; A61K 2039/52; A61K 2039/525; A23L 33/135
  See application file for complete search history.

(56) References Cited

U.S. PATENT DOCUMENTS

| | | | | |
|---|---|---|---|---|
| 2004/0192642 | A1* | 9/2004 | Yang | A61F 13/2051 514/54 |
| 2007/0116671 | A1* | 5/2007 | Prakash | A61K 9/0024 424/93.2 |
| 2013/0108607 | A1* | 5/2013 | Cowley | A61K 9/0053 424/94.4 |
| 2014/0005199 | A1* | 1/2014 | Wadee | A61K 9/0024 514/249 |
| 2014/0248396 | A1 | 9/2014 | Radecka | |

OTHER PUBLICATIONS

Priya et al.( "Enhanced Survival of Probiotic Lactabacillus acidophilus by Encapsulation with Nanostructured polyelectrolyte layers through layer-by-layer approach" in Journal of Agricultural and Food Chemistry, 2011, 11838-11845).*
de Barros et al. ("Enteric coated spheres produced by extrusion/ spheronization provide effective gastric protection and efficient release of live therapeutic bacteria" in International Journal of Pharmaceutics, Sep. 2015, available on line on Jul. 15, 2015, vol. 493, pp. 483-494).*
Nakamae, et al., Swelling behavior of hydrogels containing phosphate groups, Macromol. *Chem. Phys*, 193:983(1992).
Priva, et al., "Enhanced survival of probiotic lactabacillus acidophilus by encapsulation with nanostructured polyelectrolyte layers through layer-by-layer approach", *J Agricul Food Chem.*, 59(21):11838-45 (2011).
Reid, et al., Survival in food systems of Lactobacillus rhamnosus R011, *J Food Science*, 72(1) M31-7 (2006).
Richardson, et al., "Immersive polymer assembly on immobilized particles for automated capsule preparation", *Adv Mater.* 25(47):6874-8(2013).
Sheu, et al., "Microentrapment of lactobacilli in calcium alginate gel", *J Food Science*, 54:557-61, (1993).
Siegel, "Hydrophobic weak polyelectrolyte gels: Studies of swelling equilibria and kinetics", *Adv. Polym. Sci.* 109:233-67 (1993).
Solanki, et al., "Development of Microencapsulation Delivery System for Long-Term Preservation of Probiotics as Biotherapeutics Agent", *Biomed Res Int.* 2013:620719 (2013).
Thomas, et al., "Enhanced viability of probiotic *Saccharomyces boulardii* encapsulated by layer-by-layer approach in pH responsive chitosan-dextran sulfate polyelectrolytes", *J Food Eng.*, 136:18 (2014).
Allison, et al., "Review. Hyaluronan: a powerful tissue engineering tool", Tissue Eng., 12:2131-40 (2006).
Audet, et al., "Immobilized growing lactic acid bacteria with κ-carrageenan—locust bean gum gel", Applied Microbiol Biotech, 29(1):11-18,(1988).
Barros, et al., "Enteric coated spheres produced by extrusion/ spheronization provided effective gastric protection and efficient release of lice therapeutic bacteria", Int J Pharma., 493(1-2):483-94 (2015).
Batorsky, et al., "Encapsulation of adult human mesenchymal stem cells within collagen-agarose microenvironments", Biotechnol Bioeng. 92(4):492-500(2005).
Borgogna, et al., "Food microencapsulation of bioactive compounds: Rheological and thermal characterization of non-conventional gelling system", Food Chemistry, 122(2)416-23(2010).
Champagene, et al., "Microencapsulation for delivery of probiotics and other ingredients infunctional dairy products", Functional Dairy Products, 2:404-426 (2007).
Chen, et al., "Applications of Probiotic Encapsulation in Dairy Products", Encapsulation and Controlled Release Technologies in Food Systems, J. M. Lakkis, Ed., 4:83-112,Wiley-Blackwell, New York, NY, USA, (2007).
Cook, et al., "Layer-by-layer coating of alginate matrices with chitosan-alginate for the improved survival and targeted delivery of probiotic bacteria after oral administration", J. Mater. Chem. B, 1:52-60 (2013).
De Vos, et al., "Encapulation for preservation of functionality and targeted delivery of bioactive food components", Intl Dairy J., 20(4):292-302 (2010).
Donthidi, et al., "Effect of lecithin and starch on alginate-encapsulated probiotic bacteria", J Microencapsul., 27(1):67-77, (2010).
F'Avaro-Trindade, et al., "Microencapsulation of L. acidophilus (La-05) and B. lactis (Bb-12) and evaluation of their survival at the pH values of the stomach and in bile", J Microencapsul, 19(4):485-94, (2002).
Gentile, et al., "Polymer science for macroencapsulation of cells for central nervous system transplantation", React. Polym. 25:207-27(1995).
Haralampu, et al., "Resistant starch—a review of the physical properties and biological impact of RS3", Carbohydrate Polymers, 41(3):285-92, (2000).
Hayashi, et al., "Continuous vaccum dryer for energy saving", Drying Technology, 1(2):275-284, (1983).
Heidebach, et al., "Microencapsulation of probiotic cells by means of rennet-gelation of milk proteins", Food Hydrocolloids, 23(7):1670-7 (2009).
Heideback, et al., "Influence of casein-based microencapsulation on freeze-drying and storage of probiotic cells", J Food Engineering, 98(3):309-16 (2010).
Hu, et al., "Engineering Nanoparticle-Coated Bacteria as Oral DNA Vaccines for Cancer Immunotherapy", Nano Lett., 15(4):2732-9 (2015).
Huyghebaert, et al., "Development of an enteric-coated, layered multi-particulate formulation for ileal delivery of viable recombinant Lactococcus lactis", Eu J Pharma Biopharma, 61(3):134-41 (2005).
International Search Report and Written Opinion for corresponding PCT application PCT/US2016/065535 dated Mar. 10, 2017.
Kailasapathy, "Encapsulation technologies for functional foods and nutraceutical product development", CAB Reviews, 4(6):1-19, (2009).
Kailasapathy, et al., "Microencapsulation of probiotic bacteria: technology and potential applications", Current Issues in Intestinal Microbiology, 3(2):39-48 (2002).
King, et al., Encapsulation and Controlled Release of Food Ingredients, Sara JR and Gary AR, Eds., vol. 590 of ACS Symposium Series, 26-39, American Chemical Society, Washington, DC, USA.).
Koponen, et al., "Effect of acid stress on protein expression and phosphorylation in Lactobacillus rhamnosus GG", J. Proteomics, 75(4):1357-74 (2012).
Krasaekoopt, et al., "Evaluation of encapsulation techniques of probiotics for yoghurt", Intl Dairy J., 13(1), 3-13, 2003).
Li, et al., "The Effect of Layer-by-Layer Assembly Coating on the Proliferation and Differentiation of Neural Stem Cells", ACS Appl. Mater. Interfaces, 7(5):3018-29 (2015).
Livney, "Milk proteins as vehicles for bioactives", Curr Opin Colloid Interface Sci., 15(1-2):73-83, (2010).
Makhlof, et al., "Design and evaluation of novel pH-sensitive chitosan nanoparticles for oral insulin delivery", Eur J Pharm Sci. 18:42(5):445-51(2011).

(56) References Cited

OTHER PUBLICATIONS

Malm, et al., "Cellulose acetate phthalate as an enteric coating material", J Am Pharmal Assoc., 40(10): 520-5, (1951).
Miyata, et al., "Stimuli-sensitivities of hydrogels containing phosphate groups", Chem. Phys. 195:1111-20—(1994).
Mortazavian, et al., "Principles and methods of microencapsulation of probiotic microorganisms", Iranian J Biotech., 5(1):1-18 (2007).
Moustafine, et al.,"Comparative evaluation of interpolyelectrolyte complexes of chitosan with Eudragit L100 and Eudragit L100-55 as potential carriers for oral controlled drug delivery", Europ. J. of Pharma Biopharma., 70:215-25 (2008).

* cited by examiner

Bacteria → Chitosan Layer → Alginate Layer → (CHI/ALG)₂

PH-RESPONSIVE MUCOADHESIVE POLYMERIC ENCAPSULATED MICROORGANISMS

CROSS-REFERENCE TO RELATED APPLICATIONS

This application claims priority to U.S. Ser. No. 62/333, 570, filed May 9, 2016, and U.S. Ser. No. 62/267,121, filed Dec. 14, 2015, which are incorporated herein in their entirety.

FIELD OF THE INVENTION

The invention relates generally to microencapsulation delivery systems and in particular to the enhancement of site-specific delivery of microorganisms within the gastrointestinal tract to treat or prevent diseases and/or conditions.

BACKGROUND OF THE INVENTION

The gastrointestinal (GI) microbiome has been widely investigated for its role in many diseases, ranging from diabetes to depression to cancer. The roles of specific GI microorganisms in regulation and progression of these diseases have recently been defined and described, and as such, efforts to modulate the microbiome (e.g., decreasing disease-causing bacterial populations and increasing probiotic populations) are of particular interest. Unfortunately, technologies facilitating the controlled and direct modulation of the GI microbiome are lacking, mostly due to the challenges arising from the delivery of microbes through the stomach (e.g., low pH and high bile salt concentration) to target areas in the GI tract (e.g., intestines and colon).

WO2009070012 discloses protein-based probiotic encapsulates to enhance the survival of the probiotics. Cook, et al. used a model probiotic, *Bifidobacterium breve*, encapsulated into an alginate matrix before coating in multilayers of alternating alginate and chitosan (Cook M T et al., *J. Mater. Chem. B*, 2013, 1, 52-60). A significantly improved viability of the probiotics targeted to the intestine was observed when encapsulated. However, Cook et al encapsulated cell aggregates rather than single cells. Quorum sensing has been implicated where specific gene expressions under acidic conditions in several probiotics were observed (Koponen J et al., *J. Proteomics* 75(4):1357-1374 (2012)).

Furthermore, Cook et al developed the probiotic delivery system mainly to overcome the challenges of survival through the gastric insults of low pH and enzymatic activity. However, these systems have been relatively crude at ensuring delivery to the desired anatomical region. There exists a need for effective compositions to maintain viability of microorganisms following ingestion as well as the abilities to adhere to the target tissue(s) so that its contents will be delivered to targeted tissues as a function of proximity and duration of the contact.

Therefore, it is an objective of the current invention to provide compositions for targeting encapsulated microorganism to a specific site within the GI tract.

It is also an objective of the current invention to provide compositions of encapsulated microorganism with an improved survival and retention.

It is a further objective to control the growth of the microorganism for the intended purpose.

SUMMARY OF THE INVENTION

Compositions and methods of use for preferentially targeting therapeutic, prophylactic or diagnostic microorganisms, or antigenic components thereof, with prolonged survival to select sites within the gastrointestinal tract have been developed. The compositions may also include therapeutic, prophylactic and/or diagnostic agents.

Compositions for selectively targeting microorganisms with prolonged survival include encapsulated single-cell microorganisms, encapsulated in one or more layers of mucoadhesive polymers, coated with an outer layer of pH-responsive polymers. The pH-responsive polymers dissolve at a specific pH or range of pHs. For example, the pH or range of pH can correspond with the local pH of a specific target site which allows the release of the encapsulated microorganism at the site. Further, the layer-by-layer mucoadhesive polymeric coating prolongs viability and enhances the retention of the encapsulated microorganism so that it will not be eliminated before it has had a chance to exert an effect. In a preferred embodiment, the layer-by-layer encapsulating polymers include one or two bilayers of chitosan and/or alginate, and a pH-responsive polymer outer layer. Exemplary pH-responsive polymers include EUDRAGIT® E PO and EUDRAGIT® L100.

Methods for targeting the encapsulated microorganisms to specific locations within the GI tract are provided. Generally, the methods include administering single-cell microorganisms encapsulated in one or more layers of mucoadhesive polymers, and further coated with an outer layer of pH-responsive polymers to a subject. In some embodiments the subject is suffering from a condition associated with alteration in the gut microbiota. Such conditions include Crohn's disease, ulcerative colitis, diverticulitis, irritable bowel syndrome, gluten insensitivity, lactose intolerance, obesity, asthma, allergies, metabolic syndrome, diabetes, psoriasis, eczema, rosacea, atopic dermatitis, gastrointestinal reflux disease, cancers of the gastrointestinal tract, bacterial vaginosis, neurodevelopmental conditions and general lowered immunity following a course of antibiotics or chemotherapy. Typically, an effective dosage is administered in one or more doses, over a time period of once a day, once every other day, once a week, biweekly, etc. until one or more symptoms of the condition or disease status is improved.

BRIEF DESCRIPTION OF THE DRAWINGS

FIG. 2A shows zeta potential for each sequential layer of chitosan and alginate, and for two chitosan and alginate bilayers, (CHI/ALG)$_2$, at pH 1 and 7. FIG. 2B shows relative fluorescence of *Bacillus coagulans* coated with 2, 4 or 6 layers of fluorescent chitosan or alginate.

FIG. 3A shows the polymer release kinetics of chitosan from (CHI/ALG)$_2$ coated *Bacillus coagulans*, and FIG. 3B with shows the polymer release kinetics of alginate from (CHI/ALG)$_2$ coated *Bacillus coagulans*, with both cases being normalized to neutral PBS conditions.

FIG. 4A shows the survival rate of plain *Bacillus coagulans* under SGF insult for 30 min, 1 hr and 2 hr. FIG. 4B shows the survival rate of unmodified *Bacillus coagulans* under 4% bile insult for each of 30 min, 1 hr and 2 hr, respectively. FIG. 4C shows the survival rate of plain or LbL-formulated (CHI/ALG)$_2$ *Bacillus coagulans* in PBS, SGF and 4% bile after 2 hours incubation.

(FIG. 6A) Zeta potential for non-formulated *Bacillus coagulans* (BC), BC with sequential layer(s) of EPO and ALG including BC (EPO), BC (EPO/ALG)$_1$ and BC (EPO/ALG)$_{1.5}$ in simulated intestinal fluid (SIF). In addition, zeta potential is also shown for BC (EPO/ALG)$_{1.5}$ after exposure to simulated gastric fluid (SGF, black circle) or remaining in SIF (open squares and black diamond). (FIG. 6B) Zeta potential for non-formulated *Bacillus coagulans* (BC), BC with sequential layer(s) of L100 and chitosan (CHI) including BC (CHI), BC (CHI/L100)$_1$. In addition, zeta potential is also shown for after exposure to SGF (black diamond) or SIF (open square and black circle).

DETAILED DESCRIPTION OF THE INVENTION

Figure 1:
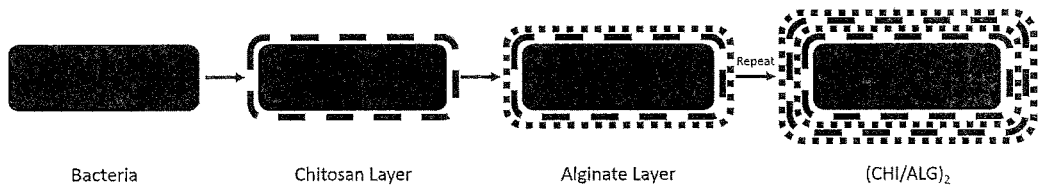
FIG. 1 is a schematic showing layer-by-layer templating of polymeric materials onto a bacterial cell.

An optimal controlled release system designed to administer beneficial microorganisms in specific areas of the gastrointestinal tract requires three critical areas of consideration: (1) protecting the beneficial microorganisms from harsh conditions such as stomach acid or bile salt to enhance their survival; (2) facilitating mucoadhesion to the lining of the appropriate viscus so that the probiotic microorganisms will not be entrained beyond the desired site of action and eliminated before it has had a chance to exert a topical effect; and (3) controlling release, for example via pH sensitive polymers so as to facilitate growth in pH-regulated areas of the GI tract.

Cell encapsulation technology has the potential to protect microorganisms and to deliver them into the gut. However, there are still many challenges to overcome with respect to the microencapsulation process and the conditions prevailing in the gut. Single cell encapsulation offers advantages such as increasing surface area for attachment at target sites as well as avoiding quorum sensing which could have negative effects on the encapsulated cells.

I. Definitions

The term "mucoadhesive" is a property of a material (e.g. a polymer or a protein) that has the ability to adhere to mucosal membranes in the aqueous environment of the gastrointestinal tract.

The term "enteric" refers to a polymer/protein coating on bacteria that facilitates safe transit (e.g. avoiding acidic or bile salt mediated death) through stomach for delivery to the small intestine and/or the colon. This can be tested by subjecting different coating formulations against specific biological insults. For example, incubating coated bacteria in acidic or bile-salt solutions at 37° C. and comparing their survival to non-coated bacteria, either by direct counting or colorimetric methods. The result will capture the enteric potential of the coating formulation.

The term "pH responsive" generally refers to a polymer/protein coating that degrades or dissolves in response to changes in the pH of its immediate surrounding. Of particular interest are coatings that are stable in acidic conditions (pH<5), but degrade in neutral conditions (pH>7) since these coatings will facilitate stability in the stomach and dissolve in the small intestines and/or colon. This can be tested by subjecting different coating formulations to solutions of varying pHs. Confirmation of layer removal can be performed by testing for surface charges (if the coated polymers are of opposite or distinct charge) or by testing the solution for labeled (e.g. fluorescent or radiolabeled) polymer that had been removed due to changes in the pH.

The terms "microbiome" or "microbiota" are used interchangeably, and refer to collectively, to the entirety of microbes found in association with a higher organism, such as a human. Organisms belonging to a human's microbiota may generally be categorized as bacteria, archaea, yeasts, and single-celled eukaryotes, as wells as various viruses and parasites such as Helminths.

The term "probiotic" utilizes the World Health Organization's 2001 definition of "live micro-organisms which, when administered in adequate amounts, confer a health benefit on the host". Probiotics must be alive when administered, have viability and reproducibility based on in vivo results, and during use and storage.

The terms "biocompatible" and "biologically compatible" generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "biodegradable", generally refers to a polymer that will degrade or erode by enzymatic action and/or hydrolysis under physiologic conditions to smaller units or chemical species that are capable of being metabolized, eliminated, or excreted by the subject. The degradation time is a function of polymer composition, morphology, such as porosity, particle dimensions, and environment.

The term "effective amount" or "therapeutically effective amount" means a dosage sufficient to alleviate one or more symptom of the disease or disorder state being treated or to otherwise provide a desired pharmacologic and/or physiologic effect. The precise dosage will vary according to a variety of factors such as subject-dependent variables (e.g., age, immune system health, etc.), the disease, and the treatment being effected.

The terms "treat", "treatment" and "treating" refer to the reduction or amelioration of the progression, severity and/or duration of a disease or disorder, delay of the onset of a disease or disorder, or the amelioration of one or more symptoms (preferably, one or more discernible symptoms) of a disease or disorder, resulting from the administration of one or more therapies (e.g., one or more therapeutic agents). The terms "treat", "treatment" and "treating" also encompass the reduction of the risk of developing a disease or disorder, and the delay or inhibition of the recurrence of a disease or disorder.

The term "enteral administration" means administration via absorption through the gastrointestinal tract. Enteral administration can include oral and sublingual administration, gastric administration, or rectal administration.

The terms "enhance", "increase", "stimulate", "promote", "decrease", "inhibit" or "reduce" are used relative to a control. Controls are known in the art. For example, an increase response in a subject or cell treated with a compound is compared to a response in subject or cell that is not treated with the compound.

The term "pharmaceutically acceptable carrier" or "pharmaceutically acceptable excipient" means one or more carrier ingredients approved by a regulatory agency of the Federal or a state government or listed in the U.S. Pharmacopoeia or other generally recognized pharmacopoeia for use in animals, mammals, and more particularly in humans.

The term "in combination" refers to the use of more than one therapeutic agent. The use of the term "in combination" does not restrict the order in which said therapeutic agents are administered to a subject.

II. Compositions

Compositions for preferentially targeting microorganisms with prolonged survival to select sites along the gastrointestinal tract generally include a beneficial microorganism associated encapsulated in one or multilayers of polymer(s). In some embodiments, the compositions are targeted to the small intestine of a subject. In other embodiments, the compositions are targeted to the colon of a subject.

Typically the composition includes encapsulating polymers that resist the physiological conditions present within the mammalian digestive tract, such as gastric acids and bile salts, to enhance the survival of the encapsulated microorganisms. A preferred agent is an organism that is non-pathogenic in humans, such as probiotic bacteria. In a preferred embodiment, the compositions include pH-responsive polymers that adhere and dissolve at targeted site within the GI tract to allow the attachment and proliferation (growth) of the encapsulated organism at the site. In further embodiments, the compositions contain encapsulating polymers that regulate the growth of the probiotic agent at the target site.

In some embodiments, multiple microorganisms are encapsulated within the same polymeric particle. In another embodiment, the encapsulated agents are live attenuated vaccines such as Type II oral poliovirus.

A. Agents to be Encapsulated

Agents to be encapsulated include probiotic microorganisms, such as bacteria and yeast, genetically transformed prokaryotic or eukaryotic cells, as well as viruses.

1. Probiotic Microorganisms

Probiotic is a term that means "for life" and defined as "live microorganisms that beneficially affect the host's health by improving its microbial balance". *Lactobacillus* and *Bifidobacteria* are the two most common types of microorganisms which are extensively used as probiotics in humans. Probiotics are different based on the species. For examples, in dogs and cats the most common probiotic organism is *Enterococcus faecium*. In ruminants, *Lactobacillus pentosus* WE7 is useful for the prevention and treatment of enteric disease in horses. The use of probiotic bacterial culture stimulates the growth of preferred microorganisms, crowds out potentially harmful bacteria, and reinforces the body's natural defense mechanisms. A non-limiting list of exemplary probiotic microorganisms includes Lactic acid bacteria (LAB), such as *Lactobacillus* spp., *Leuconostoc* spp., *Pediococcus* spp., *Lactococcus* spp., *Bifidobacterium* spp. and *Streptococcus* spp., as well as certain yeasts and bacilli. In young pre-ruminants, probiotics such as LAB or *Bacillus* species generally target the lower intestine and represent an interesting means to stabilize the gut microbiota and decrease the risk of pathogen colonization. Probiotics for adult ruminants have mainly been selected to improve fiber digestion by rumen microorganisms. Such probiotics have positive effects on various digestive processes, especially cellulolysis and the synthesis of microbial proteins. The main form of probiotic commonly used in dairy cows is various strains of yeast (mostly *Saccharomyces cerevisiae*). Regarding bacterial probiotics for adult ruminants, lactate-producing bacteria (*Enterococcus, Lactobacillus*), which sustain lactic acids are a more constant level than *Streptococcus bovis*, may represent a possible means of limiting acidosis in high-concentrate-fed animals, especially feedlot cattle. *Megasphaella elsdenii* or

*Propionibacterium* species, which utilize lactate, have also been administered as direct fed microbials to avoid the accumulation of ruminal lactate.

Some bacterial strains have been widely discussed in the literature and clinical studies have demonstrated their therapeutic effect in a human subject (Solanki H K, et al., *Biomed Res Int.* 2013: 620719 (2013)). Examples of probiotic strains and their intended therapeutic applications include *Lactobacillus plantarum* 299v, *Bacillus coagulans* ATCC no. 31284, and *Lactobacillus acidophilus* L1 for hypercholesterolemia and cardiovascular disease; *Lactobacillus rhamnosus* GG for prevention of atopy; *Lactobacillus rhamnosus* GG, *Bifidobacterium lactis*, and *Lactobacillus paracasei* for eczema; *Lactobacillus rhamnosus* GG, *Bifidobacterium lactis*, and *Lactobacillus paracasei* for food allergies; *Lactobacillus rhamnosus*, *Bifidobacterium lactis*, *Lactobacillus johnsonii*, *Lactobacillus rhamnosus*, and *Lactobacillus acidophilus* for lowered immunity; *Lactobacillus rhamnosus* GG, *Saccharomyces cerevisiae*, *Lactobacillus acidophilus*, and *Lactobacillus plantarum* 299v for antibiotic use (during and after); *Lactobacillus rhamnosus* GG for nonsteroidal anti-inflammatory drug; *Lactobacillus rhamnosus* GG, *Saccharomyces cerevisiae* for intestinal hyperpermeability; *Lactobacillus rhamnosus* GG, *Lactobacillus reuteri* MM53, *Lactobacillus paracasei* CRL431, *Lactobacillus acidophilus* CRL730, *Lactobacillus johnsonii* La1, *Bifidobacterium lactis* Bb12, *Lactobacillus plantarum* 299v, and *Lactobacillus paracasei* for gastroenteritis; *Lactobacillus johnsonii* La1α, *Lactobacillus plantarum* 299v, and *Lactobacillus rhamnosus* GG for giardia infection; *Lactobacillus rhamnosus* GG, *Lactobacillus johnsonii* La1, *Lactobacillus plantarum* 299v, *Lactobacillus paracasei*, and *propionibacterium freudenreichii* HA-101 and HA-102 for intestinal dysbiosis; *Lactobacillus acidophilus*, *Lactobacillus johnsonii* La1 for lactose intolerance; *Lactobacillus johnsonii* La1, *Lactobacillus acidophilus*, and *Lactobacillus rhamnosus* for GG for peptic ulcer disease & nonerosive gastritis; *Lactobacillus plantarum* 299v, VSL no. 3β for irritable bowel syndrome; *Lactobacillus acidophilus* NCFB 1748, VSL no. 3α for radiation-induced diarrhea; *Lactobacillus rhamnosus* GG, *Bifidobacterium lactis* Bb12, *Lactobacillus acidophilus*, *Saccharomyces cerevisiae*, and *Lactobacillus plantarum* 299v for traveller's diarrhea; *Lactobacillus rhamnosus* GG, *Saccharomyces cerevisiae* for Crohn's disease; *Escherichia coli* Nissle 1917, VSL no. 3β, *Lactobacillus plantarum* 299 for ulcerative colitis; *Lactobacillus rhamnosus* GG, *Lactobacillus acidophilus*, *Lactobacillus paracasei*, *Lactobacillus acidophilus*, and *Lactobacillus delbrueckii* ssp. *bulgaricus* strain LB-51 for prevention of colon cancer; *Lactobacillus rhamnosus* GR-1, *Lactobacillus fermentum* B-54, *Lactobacillus fermentum* RC-14, and *Lactobacillus acidophilus* for urinary tract infection; *Lactobacillus acidophilus*, *Lactobacillus rhamnosus* GG, *Lactobacillus rhamnosus* GR-1, and *Lactobacillus fermentum* RC-14 for vaginal candidiasis (thrush).

In some embodiments, the microorganisms to be delivered in a subject for general health or for helping recovery after a course of antibiotics or chemotherapy include *Lactobacillus acidophilus*, *Bifidobacterium longum*, *Bifidobacterium bifidum*, *Lactobacillus fermentum*, and *Lactobacillus rhamnosus*, *Streptococcus thermophiles*, *Bifidobacterium breve* and *Bacillus coagulans*. Total weight of microbial populations occupying different regions in the digestive tract at different pH is presented in Table 1.

TABLE 1

Microbial populations in the digestive tract of normal humans.

|  | Stomach | Jejunum | Ileum | Colon |
| --- | --- | --- | --- | --- |
| Viable bacteria per gram | $0-10^3$ | $0-10^4$ | $10^5-10^8$ | $10^{10}-10^{12}$ |
| pH | 3.0 | 6.0-7.0 | 7.5 | 6.8-7.3 |

In some embodiments, the microorganisms to be delivered in a subject for diarrhea treatment are *Lactobacillus rhamnosus*, *Lactobacillus reuteri*, and *Saccharomyces boulardii*.

In some embodiments, the microorganism to be delivered in a subject for stomach ulcer is *Bifidobacterium bifidum*.

In some embodiments, the microorganisms to be delivered in a subject for gluten insensitivity include *Lactobacillus casei*, *Lactobacillus fermentum*, *Lactobacillus parcasei*, *Lactobacillus bifidus*, and *Saccharomyces boulardii*.

In some embodiments, the microorganisms to be delivered to preterm babies include *Bifidobacterium breve*, *Saccharaomyces boulardii*, *Bifidobacteria infantis*, *Streptococcus thermophiles*, *Bifidobacterium bifidum*, *Lactobacillus acidophilus*, *Lactobacillus casei*, *Lactobacillus sporogenes*, *Lactobacillus planatarum*, *Lactobacillus rhamnosus*, and *Bifidobacterium lactis*.

In some embodiments, the compositions contain probiotics for dogs. Some exemplary microorganisms include *Interococcus faecium*, and *Bacillus coagulans* for general health; *Lactobacillus acidophilus*, and *Lactobacillus rhamnosus* for treating diarrhea. Further non-limiting examples include *Bifidobacterium animalis*, *Lactobacillus acidophilus*, *Lactobacillus rhamnosus*, *Lactobacillus salivarius*, *Lactobacillus fermentum*, and *Lactobacillus reuteri*.

In some embodiments, the disclose composition contain probiotics for horses. Some exemplary microorganisms include *Lactobacillus plantarum*, *Enterococcus faecium*, *Lactobacillus casei*, and *Lactobacillus acidophilus* as well as *Saccharomyces boulardii*, and *Lactobacillus reuteri*.

In some embodiments, the disclose composition contain probiotics for cattle. Some exemplary microorganisms include *Lactobacillus fermentum*, *Enterococcus faecium*, *Lactobacillus acidophilus*, and *Lactobacillus casei*.

In some embodiments, the disclosed composition contain probiotics for cats. Some exemplary microorganisms include *Enterococcus faecium* and *Lactobacillus acidophilus*.

Most probiotic formulations contain a mixture of one or more types of organisms. The bacteria may be in dry or lyophilized form, or sporulated.

2. Transformed or Genetically Engineered Microorganisms

Typically, the encapsulated microorganisms are live prokaryotic or eukaryotic cells. In some embodiments, the cells are a transformed or modified form of a naturally occurring strain. Methods for transforming cells are known in the art. In other embodiments, the microorganisms are bacterial spores or other senescent forms of the bacteria. When bacterial spores are used, the spores can be dormant spores. In one embodiment the spores are spores of *Bacillus subtilis*. In other embodiments, the bacteria are attenuated or otherwise non-viable bacteria, such as killed bacteria. In some embodiments the bacteria are selected for a property associated with the genotype or phenotype of the specific genus, strain or sub-strain. Exemplary characteristics include antibiotic resistance.

In some embodiments, these probiotic microorganisms are genetically engineered to be resistant to common antibiotics such as penicillins, cephaolsporins, tetracyclines, aminoglycosides, and macrolides. These can be used to complement antibiotic treatment to restore healthy microbiota.

In some embodiments, microorganisms are genetically engineered to include a reporter system. Some exemplary reporter systems include bioluminescent and fluorescent proteins such as green fluorescent proteins from jellyfish. These bacteria can be used as a diagnostic tool to detect pathological conditions within the GI tract including inflammation and ulcer.

In some embodiments, microorganisms are genetically engineered to secrete therapeutic, prophylactic or diagnostic products. For example, microorganisms are engineered to secret insulin for treating diabetes to act as living "drug factories"; or bacteria are engineered to secret fluorescent proteins for detection of defined conditions within the GI tract.

3. Vaccines

A vaccine is a biological preparation that provides active acquired immunity to a particular disease. A vaccine typically contains the same antigens (or parts of antigens) from a microorganism that causes disease. For example, measles vaccine contains measles virus. However, the antigens in vaccines are either killed, or weakened to the point that the do not cause disease but they are strong enough to stimulate the body's immune system so that the immune system can readily recognize and kill any of microorganisms that it later encounters (immunity).

An antigen can include any protein or peptide that is foreign to the subject organism. Preferred antigens can be presented at the surface of antigen presenting cells (APC) of a subject for surveillance by immune effector cells, such as leucocytes expressing the CD4 receptor (CD4 T cells) and Natural Killer (NK) cells. Typically, the antigen is of viral, bacterial, protozoan, fungal, or animal origin. In some embodiments the antigen is a cancer antigen. Cancer antigens can be antigens expressed only on tumor cells and/or required for tumor cell survival.

Instead of the entire organism, one can encapsulate one or more antigenic protein, lipid, sugar, nucleic acid, or combination thereof\, for use as a vaccine. As used herein, "antigenic" refers to the ability of the molecule to elicit a B or T cell mediated response, which may be humoral (resulting in antibody) or cell mediated (resulting in activation of dendritic cells, macrophages, T cells or the pathway resulting in activation thereof).

Certain antigens are recognized by those skilled in the art as immuno-stimulatory (i.e., stimulate effective immune recognition) and provide effective immunity to the organism or molecule from which they derive. Antigens can be peptides, proteins, polysaccharides, saccharides, lipids, nucleic acids, or combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof. Suitable antigens are known in the art and are available from commercial government and scientific sources. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. Antigens may be provided as single antigens or may be provided in combination. Antigens may also be provided as complex mixtures of polypeptides or nucleic acids.

In some embodiments, live attenuated or inactivated vaccines are incorporated within the pH-responsive mucoadhesive polymeric encapsulation. Exemplary vaccines include live, attenuated viral vaccines, such as the cold-adapted, recombinant nasal influenza and oral rotavirus vaccines, and adenovirus-based vaccine as well as the poliovirus and *Salmonella typhi* vaccines. The vaccine can include live, attenuated or inactivated microorganisms or a protein, DNA or lipid component thereof.

Suitable vaccines for encapsulation include, but are not limited to, vaccines against anthrax, chickenpox, diphtheria, hepatitis A, hepatitis B, HIB, HPV, influenza, Japanese encephalitis, measles, viral meningitis, mumps, whooping cough, pneumonia, polio, rabies, ritavirus, rubella, shingles, smallpox, tetanus, tuberculosis, typhoid, and yellow fever. These are typically in the form of attenuated organisms, although isolated proteins can also be incorporated.

Antigenic molecules can be encapsulated alone, or in combination with microorganisms, which may be present in an amount effective as an adjuvant to enhance the immune response, or to broaden the response.

4. Therapeutic, Prophylactic and Diagnostic Agents

Other agents may also be incorporated with the microorganisms and/or components thereof. Representative agents may be proteins, lipids, sugars, nucleic acid molecules, or combinations thereof, small molecule drugs (typically less than 1000 Da although some may be higher), or radiopaque, radionuclide, or magnetic imaging agents.

Other therapeutic, nutritional, prophylactic or diagnostic agents can also be included. In one embodiment, antiparasitic agents are incorporated into the particles. Antiparasitic agents, such as anti-protozoa agents, antihelminthics, and combinations thereof, include, but are not limited to, antinematodes, anticestodes, antitrematodes, antiamoebics, antiprotozoals, and combinations thereof.

Suitable antinematodal drugs include, but are not limited to, benzimiadazoles (e.g., mebendazole, thiabendazole), avermectins (e.g., ivermectin), pyrantel pamoate, diethylcarbamazine, and combinations thereof.

Suitable anticestodes include, but are not limited to, niclosamine, praziquantel, albendazole, and combinations thereof.

Suitable antitrematodes include, but are not limited to, praziquantel.

Suitable antiamoebics include, but are not limited to, rifampin, amphotericin B, and combinations thereof.

Suitable antiprotozoals include, but are not limited to, melarsoprol, eflornithine, metronidazole, tinidazole, miltefosine, and combinations thereof.

The particles can contain one or more antiviral and/or antimicrobial agents. Suitable agents include anti-influenza agents, anti-poliovirus agents, antihepatitis agents, anti-arboroviral agents (anthropod-borne viruses such as dengue fever, yellow fever, and malaria), anti-rotavirus agents, anti-Ebola virus agents, anti-Marburg virus agents, anti-Lassa virus agents, and combinations thereof. Suitable antimicrobial agents include, but are not limited to, anti-cholera agents, anti *E-coli* agents, anti-tuberculosis agents, antileprosy agents, and combinations thereof.

Exemplary micronutrients include, but are not limited to, iron, cobalt, zinc, manganese, copper, iodine, selenium, molybdenum, chromium, vitamin A, beta carotene, vitamin B1, vitamin B2, vitamin B3, vitamin B6, vitamin B9 (folic acid), vitamin B12, vitamin C, vitamin D3, vitamin E, vitamin K, pantothenic acid, biotin, and combinations thereof. The required daily dosage of most micronutrients is less than 100 mg/day.

Different agents, and different combinations of agents, can be combined in the same particle, different particles, or combinations thereof. This can be done for reason of convenience, such as having separate particles for different agents for convenience in combining or mixing different agents in different formulations, or in order to increase or optimize the stability or form of the agents based on the composition of the particle.

B. Biomaterials for Microencapsulation

The biomaterials used for microorganism encapsulation include polymers, such as natural polymers and synthetic polymers (Gentile F T et al., *React. Polym.* 25:207-227 (1995)). The terms biocompatible and biodegradable are associated with many of these biomaterials. Biomaterials for microorganism encapsulation are in direct contact with the living cells. Issues involved when selecting biomaterials for microorganism encapsulation are: (a) physicochemical properties (chemical composition, morphology, mechanical strength, stability in gastric and intestinal fluids); (b) toxicology assay; (c) manufacturing and sterilization processes.

Biomaterials are inorganic or organic macromolecules, consisting of repeated chain of monomers linked by covalent bonds. Their chemical structure and the conformation of the monomer chains give them specific functionality such as ability to form gels. The most common biomaterial used for microorganism encapsulation is alginate. Other supporting biomaterials include carrageenan, gelatin, chitosan, whey proteins, cellulose acetate phthalate, locust bean gum and starches (Solanki H K, et al., *Biomed Res Int.* 2013: 620719 (2013)).

Exemplary gastric resistant natural polymers include, but are not limited to, pectin and pectin-like polymers which typically consist mainly of galacturonic acid and galacturonic acid methyl ester units forming linear polysaccharide chains. Typically these polysaccharides are rich in galacturonic acid, rhamnose, arabinose and galactose, for example the polygalacturonans, rhamnogalacturonans and some arabinans, galactans and arabinogalactans. These are normally classified according to the degree of esterification.

In high (methyl) ester ("HM") pectin, a relatively high portion of the carboxyl groups occur as methyl esters, and the remaining carboxylic acid groups are in the form of the free acid or as its ammonium, potassium, calcium or sodium salt. Useful properties may vary with the degree of esterification and with the degree of polymerization. Pectin, in which less than 50% of the carboxyl acid units occur as the methyl ester, is normally referred to as low (methyl) ester or LM-pectin. In general, low ester pectin is obtained from high ester pectin by treatment at mild acidic or alkaline conditions. Amidated pectin is obtained from high ester pectin when ammonia is used in the alkaline deesterification process. In this type of pectin some of the remaining carboxylic acid groups have been transformed into the acid amide. The useful properties of amidated pectin may vary with the proportion of ester and amide units and with the degree of polymerization.

In one embodiment, the gastric resistant natural polymer is pectin. The gastric resistant natural polymer is present in an amount less than about 5% by weight of the composition, preferably from about 2 to about 4% by weight of the composition.

1. Mucoadhesive Polymers

The presence of a mucus layer that covers the surface of a variety of organs has been capitalized to develop mucoadhesive, or bioadhesive dosage forms that remain in the administration site for prolonged times, increasing the local and/or systemic bioavailability of the administered drug. The benefit of the incorporation of mucoadhesive polymers into the structure of pharmaceutical products is to prolong their residence time in the targeted site and to allow the release of the drug cargo.

Suitable polymers that can be used to form bioadhesive dosage include soluble and insoluble, non-biodegradable and biodegradable polymers. These can be hydrogels or thermoplastics, homopolymers, copolymers or blends, natural or synthetic. In preferred embodiments, the polymers have a bioadhesive force that can effectively and specifically target and bind the mucosal surface of the host. An exemplary bioadhesive polymer can bind to one or more mucosal surfaces of a host with a force of between 110 N/m$^2$ (11 mN/cm$^2$) and 100,000 N/m$^2$.

The mucosal surface layer of the host varies from species to species and even amongst different animals due to differences arising from variations in diet, location, GI activity, sex and state of health. In general, GI mucus is made of 95% water and 5% electrolytes, lipids, proteins and glycoproteins, as described by Spiro, R. G., "Glycoproteins," *Annual Review of Biochemistry*, 39, 599-638, 1970; Labat-Robert, J. & Decaeus, C., "Glycoproteins du Mucus Gastrique: Structure, Function, et Pathologie," *Pathologie et Biologie* (Paris), 24, 241 (1979). However, the composition of the latter fraction can vary greatly. Proteins, including the protein core of the glycoproteins, can made up anywhere from 60 to 80% of this fraction. Horowitz, M. I., "Mucopolysaccharides and Glycoproteins of the Alimentary Tract" in *Alimentary Canal* (eds. C. F. Code), pp. 1063-1085 (Washington: American Physiological Society, 1967). The glycoproteins typically have a molecular weight of approximately two million and consist of a protein core (approximately 18.6-25.6% by weight) with covalently attached carbohydrate side chains (approximately 81.4-74.4% by weight) terminating in either L-fucose or sialic acid residues. Spiro, R. G., "Glycoproteins," *Annual Review of Biochemistry*, 39, 599-638, 1970; Scawen, M. & Allen, A., "The Action of Proteolytic Enzymes on the Glycoprotein from Pig Gastric Mucus," *Biochemical Journal*, 163, 363-368, 1977; Horowitz, M. I. & Pigman, W., *The Glycoconjugates*, pp. 560 (New York: Academic Press, Inc., 1977); Pigman, W. & Gottschalk, A., "Submaxillary Gland Glycoproteins" in *Glycoproteins: Their Composition, Structure and Function* (eds. A. Gottschalk), pp. 434-445 (Amsterdam: Elsevier Publishing Company, Inc., 1966). Species and location differences in the composition of these glycoproteins have been reported by Horowitz, M. I., "Mucopolysaccharides and Glycoproteins of the Alimentary Tract" in *Alimentary Canal* (eds. C. F. Code), pp. 1063-1085 (Washington: American Physiological Society, 1967).

In order for bioadhesive particles to embed themselves in the mucus lining the GI tract, the radius of the individual particles should be as thick as the thickness of the natural mucous layer. It has been shown that the gastric mucous layer thickness typically varies from 5 to 200 μm in the rat and 10 to 400 μm in man. Occasionally, however, it can reach thicknesses as great as 1000 μm in man, as described by Spiro, R. G., "Glycoproteins," *Annual Review of Biochemistry*, 39, 599-638, 1970; Labat-Robert, J. & Decaeus, C., "Glycoproteins du Mucus Gastrique: Structure, Fonction, et Pathologie," *Pathologie et Biologie* (Paris), 24, 241, 1979; Allen, A., Hutton, D. A., Pearson, J. P., & Sellers, L. A., "Mucus Glycoprotein Structure, Gel Formation and Gastrointestinal Mucus Function" in Mucus and Mucosa, Ciba Foundation Symposium 109 (eds. J. Nugent & M. O'Connor), pp. 137 (London: Pitman, 1984). Obvious physical differences in the mucus thickness were observed in the studies described herein. For example, the mucous layers in the rat and monkey were substantially thinner than those observed in the pig and sheep. Although the general order of adhesiveness was maintained throughout the studies, it must be noted that the tenacity of adhesion was dependent on the abundance of mucus.

Two classes of polymers appear to have potentially useful bioadhesive properties: hydrophilic polymers and hydrogels. In the large class of hydrophilic polymers, those containing carboxylic groups (e.g., poly[acrylic acid]) exhibit the best bioadhesive properties. One could infer that polymers with the highest concentrations of carboxylic groups should be the materials of choice for bioadhesion on soft tissues. In other studies, the most promising polymers were: sodium alginate, carboxymethylcellulose, hydroxymethylcellulose and methylcellulose. Some of these materials are water-soluble, while others are hydrogels. Hydrogels have often been used for bioadhesive drug delivery; however, one big drawback of using hydrogels is the lack of long-term stability during storage which is a problem for therapeutic applications.

Rapidly bioerodible polymers such as poly[lactide-co-glycolide], polyanhydrides, polyorthoesters—which would expose carboxylic groups on the external surface as their smooth surface erodes—are excellent candidates for bioadhesive drug delivery systems in the gastrointestinal tract. Biodegradable polymers are more stable than hydrogels. In addition, polymers containing labile bonds, such as polyanhydrides and polyesters, are well known for their hydrolytic reactivity. Their hydrolytic degradation rates can generally be altered by simple changes in the polymer backbone.

Representative natural polymers are proteins, such as zein, serum albumin, or collagen, and polysaccharides, such as cellulose, dextrans, and alginic acid. Representative synthetic polymers include polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, alkyl cellulose, hydroxyalkyl celluloses, cellulose ethers, cellulose esters, nitrocelluloses, polymers of acrylic and methacrylic esters, poly[lactide-co-glycolide], polyanhydrides, polyorthoestersblends and copolymers thereof. Specific examples of these polymers include cellulose acetate, cellulose propionate, cellulose acetate butyrate, cellulose acetate phthalate, carboxymethyl cellulose, cellulose triacetate, cellulose sulphate, poly(methyl methacrylate), (poly (ethyl methacrylate), poly(butyl methacrylate), Poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene and polyvinylpyrrolidone, polyurethane, polylactides, poly(butyric acid), poly(valeric acid), poly[lactide-co-glycolide], polyanhydrides, polyorthoesters, poly(fumaric acid), and poly(maleic acid).

These polymers can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif.

In some embodiments, milk proteins are natural vehicles for probiotic or other microorganism, and owing to their structural and physicochemical properties, they can be used as a delivery system (Livney Y D, Current Opinion in Colloid and Interface Science, 15(1-2):73-83, (2010)). In other embodiments, whey proteins are used for encapsulate microorganism in the current invention. Applications of whey proteins are also extended to other foods for protection during processing as well as stability during storage but also in nutraceutical for protection and soil release in the GI tract (Reid A A, et al., Journal of Food Science, 72(1) M31-M37 (2006)).

In a particular embodiment, positively-charged hydrogels, such as chitosan, are first applied onto the microorganism, followed by negatively charged hydrogels, such as alginate that exposes carboxylic groups on the surface. The rationale behind this choice is the fact that most cell membranes are actually negatively charged and there is still no definite conclusion as to what the most important property is in obtaining good bioadhesion to the wall of the gastrointestinal tract.

In a further embodiment, two sequential bilayers of alginate and chitosan are applied onto the microorganism for enhanced stability and adhesion. Polyanhydrides are good candidates for bioadhesive delivery systems since, as hydrolysis proceeds, more and more carboxylic groups are exposed to the external surface. Polylactides erode by bulk erosion; furthermore, the erosion is slower. In designing these systems as bioadhesive polymers, polymers that have high concentrations of carboxylic acid were preferred.

Some non-limiting exemplary biomaterials for encapsulating probiotic agents are listed below.

i. Alginate

Alginate is a naturally derived polysaccharide extracted from various species of algae and composed of two monosaccharide units: α-L-guluronic acid (G) and β-D-mannuronic acid (M) linked from β (1-4) glycosidic bond (Formula I). M/G ratios determine the technological functionality of alginate. The gel strength depends upon high proportion block G. High temperature (60° C. to 80° C.) is needed to dissolve alginate in water. Alginate gels are insoluble in acidic media. Alginate is mostly used in concentration range of 0.5-4% (Sheu T Y et al., Journal of Food Science, 54:557-561, (1993))

Alginate can be purchased form commercially available sources such as Sigma Chemical Co., St. Louis, Mo. (#A7003).

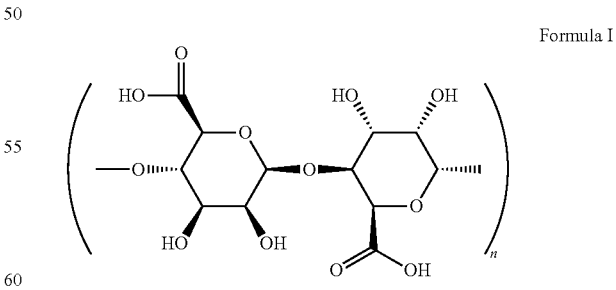

Formula I ii. Chitosan

Chitosan is a linear polysaccharide with positive charge arising from its amine groups obtained by deacetylation of chitin. It can be isolated from crustacean shells, insect cuticles, and the membranes of fungi. It is a copolymer of two monomer residues anhydro-N-acetyl-D-glucosamine and anhydrous-D-glucosamine (Formula II). It is soluble at pH<6 and forms gel structure by ionotropic gelation. Chitosan can further polymerize by means of cross-linking formation in the presence of anions and polyanions (Klein J et al., *European Journal of Applied Microbiology and Biotechnology*, 18(2):86-91, 1983). It is used for coating of gelatin capsules, because its efficiency for the increasing viability of probiotic cells is not satisfactory; it is most often used as coat/shell but not capsule.

Chitosan can be purchased from commercially available sources such as Sigma Chemical Co., St. Louis, Mo. (#448877).

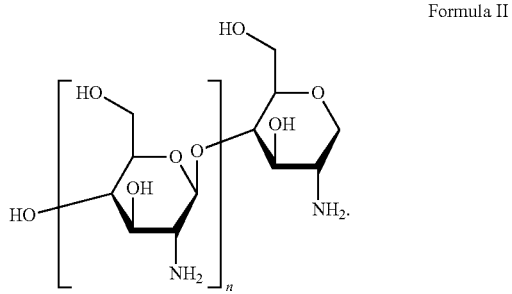

Formula II iii. Agarose

Agarose is a polysaccharide derived from seaweed used for microencapsulation of cells and the cell/agarose suspension can be modified to form microbeads by reducing the temperature during preparation. Batorsky A et al reported a system to encapsulate adult human mesenchymal stem cells (hMSC) within spherical three-dimensional (3D) microenvironments consisting of a defined mixture of collagen Type I and agarose polymers (Batorsky A et al., *Biotechnol Bioeng*. 92(4):492-500 (2005)).

iv. Starch

Starch consists of D-glucose unit joint together with glycosidic bonds. It has been used as a material for coating of alginate capsules. High-amylose corn starch (HACS) can be applied for enhancing functions of capsule or shell/coat formation. Lyophilized corn starch (LCS) has been reported to be used as capsule-forming material; however, it decomposes after being subjected to pancreatic enzymes. Resistant starch (RS) is not degraded by the pancreatic amylase. His specification apart from giving the microbeads good enteric delivery characteristic also gives them probiotic functionality as they can be used by the probiotic bacteria in the intestine (Haralampu S G et al., *Carbohydrate Polymers*, 41(3):285-292, (2000)). The incorporation of Hi-*Maize* starch improved the encapsulation of viable bacteria compared with the bacteria encapsulated without starch (Malm C J et al., *Journal of the American Pharmaceutical Association*, 40(10): 520-525, (1951)).

v. Xanthan-Gellan Gum

Gellan gum is an anionic polysaccharide derived from *Sphingomonas elodea* which is constituted of a repeating unit of four monomers that are glucose, glucuronic acid, glucose, and rhamnose. Xanthan is an exopolysaccharide derived from *Xanthomonas campestris*. The optimum mixing proportion for xanthan-gellan gum is 1:0.75 (Borgogna M et al., *Food Chemistry*, 122(2)416-423 (2010)). This mixture is resistant to acidic conditions.

vi. Guar Gum

Guar gum, also called guaran, is a galactomannan. It is primarily the ground endosperm of guar beans. The guar seeds are dehusked, milled and screened to obtain the guar gum. Guar gum is a polysaccharide composed of the sugars galactose and mannose. The backbone is a linear chain of beta 1,4-linked mannose residues to which galactose residues are 1,6-linked at every second mannose, forming short side-branches.

Guar gum is stable in solution over pH range 5-7. Strong acids cause hydrolysis and loss of viscosity, and alkalies in strong concentration also tend to reduce viscosity. It is insoluble in most hydrocarbon solvents. The viscosity attained is dependent on time, temperature, concentration, pH, rate of agitation and practical size of the powdered gum used. The lower the temperature lower the rate at which viscosity increases and the lower the final viscosity.

vii. κ-Carrageenan

Carrageenan is polymer having linear structure consisting of D-galactose units alternatively linked by α-(1-3) and β (1-4) bonds. Types of carrageenan are kappa (κ), iota (ι), and lambda (λ). Monosulfated κ-carrageenan and bisulfated ι-carrageenan contain oxygen bridge between 3 and 6 of the D-galactose, which is responsible for the conformational transition and gelatin. The λ-carrageenan is trisulfated and does not have this bridge required for gel formation. Carrageenan gelatin is induced by temperature changes. A rise in temperature (60-80° C.) is required to dissolve it, and gelation occurs by cooling to room temperature, and then microparticles are stabilized by adding potassium ion. It is commonly used as a food additive; its safety has been approved by several government agencies including FDA, Codex Alimentarius, and the joint FAO/WHO food additive. It has good capacity to form gels that can entrap the cell. However, the cell slurry should be added to the heat sterilized suspension between 40-45° C.; otherwise the gel hardens at room temperature. Usually it is used in concentration such as 2-5% (Klien J et al., *Comprehensive Biotechnology*, M. Moo-Yong, C. L. Cooney, and A. E. Humphery, Eds., pp. 542-550, Pergamon Press, Oxford, UK, 1985.). The encapsulation of probiotic cell in κ-carrageenan beads keeps the bacteria in a viable state [169], but the produced gels are brittle and do not withstand stresses (Chen M J, et al., *Encapsulation and Controlled Release Technologies in Food Systems*, J. M. Lakkis, Ed., pp. 83-107, Wiley-Blackwell, New York, N.Y., USA, 2007).

viii. Gelatin

Gelatin is used as a thermally reversible gelling agent for encapsulation. Because of its amphoteric nature, it is an excellent candidate to incorporate with anionic gel-forming polysaccharides, such as gellan gum. It is frequently used in food and pharmaceutical industries. It is a protein derived by partial hydrolysis of collagen of animal origin. It has versatile functional properties, and forms a solution of high viscosity in water which set to a gel on cooling.

ix. Hyaluronic Acid

Hyaluronic acid (HA) is a non-sulphated glycosaminoglycan (GAG) in the extracellular matrix (ECM) of many soft connective tissues, composed of alternating units of D-glucuronic acid and N-acetyl-D-glucosamine, linked together via alternating β-1,4 and β-1,3 glycosidic bonds (Garg H G et al., Chemistry and biology of hyaluronan. Elsevier Ltd.; Oxford: (2004)). HA is an attractive building block for the fabrication of artificial matrices for tissue engineering because it is biocompatible, biodegradable, bioactive, non-immunogenic and non-thrombogenic (Laurent T C E, The Chemistry, Biology, and Medical Applications of Hyaluronan and Its Derivatives. Portland Press; Miami: 1998). Efficient, biocompatible and chemo-selective cross-linking chemistries have enabled the encapsulation of cells during gelation, giving rise to three dimensional (3D) cell/gel constructs with intimate cell-matrix interactions (Allison D D, et al., *Tissue Eng.* 12:2131-2140 (2006)).

x. Pectin

The pectins, which are most abundant in the plant primary cell walls and the middle lamellae, are a class of molecules defined by the presence of galacturonic acid. The pectic polysaccharides include the galacturonans (homogalacturonan, substituted galacturonans, and RG-II) and rhamnogalacturonan-I. Galacturonans have a backbone that consists of alpha-1,4-linked galacturonic acid.

xi. Cellulose and Cellulose Derivatives

Cellulose is the most abundant naturally occurring polymer of glucose, found as the main constituent of plants and natural fibers such as cotton and linen. Some bacteria (e.g., *Acetobacter xylinum*) are also able to synthesize cellulose. Most water-soluble cellulose derivatives are obtained via etherification of cellulose, which involves the reaction of the hydroxyl groups of cellulose with organic species, such as methyl and ethyl units. The degree of substitution, defined as the average number of etherified hydroxyl groups in a glucose unit, can be controlled to a certain extent, in order to obtain cellulose derivatives with given solubility and viscosity in water solutions. Cellulose-based hydrogels, either reversible or stable, can be formed by properly crosslinking aqueous solutions of cellulose ethers, such as methylcellulose (MC), hydroxypropyl methylcellulose (HPMC), Hydroxypropyl cellulose (HPC), ethyl cellulose (EC), hydroxyethyl cellulose (HEC), carboxymethyl cellulose (CMC) and sodium carboxymethylcellulose (NaCMC), which are among the most widely used cellulose derivatives. The excellent biocompatibility of cellulose and cellulose derivatives has prompted the large use of cellulose-based devices in biomedical applications.

2. Enteric/pH-Response Polymers

The environmental conditions of each section along the GI tract can be exploited to design adequate delivery systems. The GI tract consists of esophagus, stomach, small intestine, and large intestine (colon). Stomach is where majority of digestion occurs. The small intestine comprised of duodenum, jejunum, and ileum and is where digestion and the majority of absorption of food/nutrients/vitamins take place. Colon is where water gets absorbed the rest is excreted as waste in the form of feces. The viable microbial populations in the digestive tract of normal humans are about $0\text{-}10^3$ for stomach, $0\text{-}10^4$ for jejunum, $10^5\text{-}10^8$ for ileum and $10^{10}\text{-}10^{12}$ for colon.

The intraluminal pH is rapidly changed from highly acid in the stomach to about pH 6 in the duodenum. The pH around esophagus is about 7.0 and drops to 1-2.5 in the stomach. The pH gradually increases in the proximal small intestine from pH 6.2-7.4 to about pH 6.8-7.9 in the distal intestine. The pH drops to 5.2 to 6.7 in the ascending colon, but again gradually increases, reaching pH 5.2-7.0 in the descending colon (Fallingborg J, *Dan Med Bull.* 46(3):183-96 (1999)). Physiology of the GI tract is an important consideration in the probiotic encapsulation process.

In some embodiments the release of the encapsulated agent is triggered by a change in pH. Numerous methods have been described in the art to enable general delivery of drugs to the colon, and any of them can be combined to improve delivery to a niche in the colon. Such methods include pH-sensitive formulations (e.g. formulations coated with enteric polymers that release drug when the pH move towards a more alkaline range, after passage through the stomach), formulations that delay the release of the drug for a lag time of 3-5 hours, roughly equivalent to small intestinal transit time, thereby securing delivery to the colon, drugs coated with bioadhesive polymers that selectively provide adhesion to the colonic mucosa (e.g. see U.S. Pat. No. 6,368,586), and delivery systems that incorporate protease inhibitors to prevent proteolytic activity in the gastrointestinal tract from degrading biologic drug agents.

In some embodiments, polymeric delivery systems with a dissolution threshold in the range of 6.8 to 7.5 are used to exploit the natural shift towards a more alkaline pH in the distal sections of the gut for colonic delivery.

Ionisable polymers with a pKa value between 3 and 10 are candidates for pH-responsive systems (R. A. Siegel, *Adv. Polym. Sci.* 109: 233(1993)). Weak acids and bases like carboxylic acids, phosporic acid and amines, respectively, exhibit a change in the ionisation state upon variation of the pH. This leads to a conformational change for the soluble polymers and a change in the swelling behaviour of the hydrogels when these ionisable groups are linked to the polymer structure.

Classical monomers are acrylic acid (AAc), methacrylic acid (MAAc), maleic anhydride (MA), and N,N-dimethylaminoethyl methacrylate (DMAEMA). But also polymers containing phosphoric acid derivatives have been reported (Nakamae K, et al., *Chem.* 193:983 (1992); Miyata T, et al., *Chem. Phys.* 195:1111 (1994)).

Some pH-responsive polymers include cationic polymers such as poly(ethylene imine) (PEI), PAMAM and other dendrimers, poly(N,N-dimethylaminoethyl methacrylate) (PDMAEMA), poly(amido amine)s, poly(L-lysine) (PLL) or modified chitosan.

In some embodiments, the pH-responsive polymer is hydroxypropyl-methylcellulosephthalate (HPMCP). In some embodiments, non-pH responsive polymers are modified with pH responsive polymers for incorporating such properties in the coating material. For example, chitosan is formulated by ionic cross-linking with HPMCPP for acid stability (Makhlof A et al., *Eur J Pharm Sci.* 18; 42(5):445-51 (2011)).

In some embodiments, the pH-responsive polymers are hydrazine, acetal, ortho-ester, and vinyl-ester functionalized polymers.

Some further exemplary pH responsive polymers are listed below.

i. EUDRAGIT® Polymers

EUDRAGIT® polymers are available from EVONIK. They are poly(methacrylate) polymers or copolymers. Examples include:

Amino alkyl methacrylate copolymers R=—CO—O—CH$_2$—CH$_2$N(CH$_3$)$_2$ for immediate release Methacrylic acid copolymers R=COOH for Delayed release Ammonioalkyl methacrylate copolymers R=CO—OCH$_2$—CH$_2$N(CH$_3$)3+Cl—for Time-controlled release Methacrylic ester copolymers R=CO—OCH$_3$ for Time-controlled release.

EUDRAGIT® L and S polymers can be used for targeting specific areas of the intestine. These polymers include Eudragit® L 30 D-55, L 100-55, L 100 and L 12,5 as well as EUDRAGIT® S 100, S 12,5 and FS 30D. In addition, different grades can be combined with each other to adjust the dissolution pH in order to achieve the required GI targeting for the encapsulated content.

EUDRAGIT® E polymers can also be used for pH sensitive release. Various cationic EUDRAGIT® E grades with dimethyl-aminoethyl methacrylate as functional group can be used for protective coatings. Some examples are EUDRAGIT® E 100, E 12,5 and E PO.

In one embodiment, the probiotic organism is coated with multilayers of EUDRAGIT® E PO and alginate where the exposure to low pH triggers the dissolution of the outer coating of Eudragit® E PO.

In another embodiment, the probiotic organism is coated with multilayers of chitosan and Eudragit® L 100 where the exposure to neutral pH triggers the dissolution of the outer coating of Eudragit® L 100.

ii. Cellulose Acetate Phthalate (CAP)

Because of its safe nature, CAP is used for controlling drug release in the intestine (Mortazavian A, et al., *Iranian Journal of Biotechnology*, 5(1)1-18, 2007). It is not soluble at pH less than 5 but it is soluble at pH higher than 6. This property is essential for probiotic encapsulation because the bilateral must not dissolve in the stomach but only in the gut. The disadvantage of CAP is that it cannot form gel beads by ionotropic gelation so capsules have been developed by emulsification. CAP is widely used as a coating agent because it provides better protection for microorganisms in simulated GI conditions (F'avaro-Trindade C S, et al., *Journal of Microencapsulation*, 19(4):485-494, (2002)). Other cellulose esters with similar properties include cellulose acetate and cellulose acetate butyrate and are widely used for preparing pH sensitive and semi-permeable microporous membranes.

C. Additional Functional Groups

In some embodiments, the encapsulated microorganism include one or more additional functional groups. One or more additional functional groups can be added to the polymeric coating, using any protocols known in the art, for example, covalent attachment (MacDonald C et al., *J R Soc Interface*. 5(23): 663-669 (2008)). In some embodiments, the additional functional groups are attached to the surface of the encapsulated microorganism directly. Exemplary functional groups include targeting elements, immunomodulatory elements, chemical groups, biological macromolecules, and combinations thereof.

1. Targeting Elements

The encapsulated microorganism can include targeting moieties that enhance attachment at targeted sites along the GI tract. Exemplary targeting elements include proteins, peptides, nucleic acids, lipids, saccharides, or polysaccharides that bind to one or more targets associated with cell, or extracellular matrix, or specific type of tumor or infected cell. The degree of specificity with which the delivery vehicles are targeted can be modulated through the selection of a targeting molecule with the appropriate affinity and specificity. For example, antibodies, or antigen-binding fragments thereof are very specific.

Typically, the targeting moieties exploit the surface-markers specific to a group of cells to be targeted. In some embodiments, immunological components of the gut wall are targeted during gut inflammation under conditions such as neoplasia, IBD, infections, autoimmune diseases (e.g. celiac disease), ischaemia-reperfusion, intestinal hypoperfusion, and e.g. the use of non-steroidal anti-inflammatory drugs. For example, calprotectin, also known as MRP-8/MRP-14 or S100A8/A9 complex plays a regulatory role in the inflammatory process. It constitutes about 60% of the soluble proteins in human neutrophilic cytosol and is also found in monocytes, macrophages, and ileal tissue eosinophils. Antibody against calprotectin allows targeting of the encapsulated microorganism to the site of inflammation.

In some embodiments the targeting domain can enhance site-specific delivery of the encapsulated microorganism to cancer cells in the GI tract.

Antibodies that function by binding directly to one or more epitopes, other ligands or accessory molecules at the surface of the GI tract, are described. Typically, the antibody or antigen binding fragment thereof has affinity for a receptor at the surface of a specific cell type, such as a receptor expressed at the small intestine.

Any specific antibody can be used in the methods and compositions provided herein. For example, antibodies can include an antigen binding site that binds to an epitope on the target cell. Binding of an antibody to a "target" cell can enhance site-specific attachment to the target cell protein via one or more distinct mechanisms.

In some embodiments, the antibody or antigen binding fragment binds specifically to an epitope. The epitope can be a linear epitope. The epitope can be specific to one cell type or can be expressed by multiple different cell types. In other embodiments, the antibody or antigen binding fragment thereof can bind a conformational epitope that includes a 3-D surface feature, shape, or tertiary structure at the surface of the target cell.

Some further non-limiting examples include targeting the disclosed composition to the disease sites for therapeutic and/or diagnostic purposes. Exemplary conditions within the GI tract include ulcer, inflammation, and cancers.

In some embodiments, a protein that is capable of specifically binding to receptors, either basally expressed or expressed on pathological cells, at the GI tract can be attached via covalent or non-covalent interactions to the surface of the encapsulated microorganism. For example, ICAM-1 and VCAM-1 proteins can bind to ICAM and VCAM receptors, respectively. ICAM and VCAM receptors are overexpressed on the inflamed intestine tissues whereas an antibody such as IgG can be used to bind to basally expressed Fc-receptors on intestine tissues.

Confirming the functionality of the incorporated protein/antibody can be done using ELISAs, or cell-binding assays (e.g. anti-ICAM functionalized bacteria can be tested for their binding ability to cells overexpressing ICAM receptor, such as LPS-stimulated HUVECS)

In some embodiments, anti-ICAM-1 is incorporated onto the surface of the encapsulated microorganism for targeting ICAM receptor at inflammation sites of the intestine tissues. The protein ICAM is overexpressed on inflamed tissues on the intestine. By including anti-icam-1 antibody at the terminal layer in the encapsulated microorganism formulation, it provides a direct means to target to the inflammation site. In some embodiments, the engineered microorganisms carrying genes for fluorescent or bioluminescent proteins are used for detection. In other embodiments, diagnostic markers such as fluorescent proteins are crossed-linked onto the encapsulated microorganism.

In some embodiments, anti-VCAM-1 is incorporated onto the encapsulated microorganism for targeting VCAM receptor at inflammation sites of the intestine tissues. Other examples include IgG for targeting basal Fc-neonatal receptors in intestine and anti-VPAC1 for targeting VPAC1 in the intestines.

In some embodiments, the target is ulcers in the stomach.

2. ImmunoModulatory Elements

Cationic polymers for use in formation of encapsulated microorganism can include immuno-modulatory factors. Exemplary immunomodulatory factors include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), corticosteroids (prednisone, dexamethasone, hydrocortisone), CRM197 (diphtheria toxin), outer membrane protein complex from *Neisseria meningitides*, as well as viral hemagglutinin and neuraminidase.

In certain embodiments, the cationic polymers include immuno-stimulatory factors. Exemplary immuno-stimulatory factors include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A.

D. Formulations

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, desintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.: Williams and Wilkins, 1995) which provides information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert), or the like. For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, Pa.: Williams & Wilkins, 1995).

A preferred method for preparing extended release tablets is by compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

1. Excipients

In addition to a therapeutic or prophylactic agent (or possibly other desired molecules for delivery), the particles can include excipients such as a sugar, such as lactose, a protein, such as albumin, and/or a surfactant.

E. Enteral Administration

The compositions are generally formulated for oral delivery.

1. Additives for Oral Administration

Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present active compounds and derivatives. See, e.g., Remington's Pharmaceutical Sciences, 18th Ed. (1990, Mack Publishing Co., Easton, Pa. 18042) pages 1435-1712. The compositions may be prepared in liquid form, or may be in dried powder (e.g., lyophilized) form. Liposomal or proteinoid encapsulation may be used to formulate the compositions (as, for example, proteinoid microspheres reported in U.S. Pat. No. 4,925,673). Liposomal encapsulation may be used and the liposomes may be derivatized with various polymers (e.g., U.S. Pat. No. 5,013, 556). See also Marshall, K. In: Modern Pharmaceutics Edited by G. S. Banker and C. T. Rhodes Chapter 10, 1979.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

2. Chemically Modified Forms for Oral Dosage

The disclosed compositions can be chemically modified so that oral delivery of the derivative is efficacious. Generally, the chemical modification contemplated is the attachment of at least one moiety to the component molecule itself, where said moiety permits (a) inhibition of degradation; and (b) uptake into the blood stream from the stomach or intestine. Also desired is the increase in overall stability of the component or components and increase in circulation time in the body. PEGylation is a preferred chemical modification for pharmaceutical usage. Other moieties that can be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane (see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189).

III. Methods of Making

In some embodiments, the microorganisms are encapsulated by extrusion, emulsion, and spray drying. In these methods, microorganisms are entrapped in the gel matrix using different gel forming mechanisms (Champagene C P et al., *Functional Dairy Products*, 2:404-426, (2007)). The encapsulating conditions are designed to maintain cell viability, and solvents involved in the encapsulation technology must be nontoxic. The ability of microorganisms to survive and multiply in the host strongly influences their probiotic benefits.

Microencapsulation techniques are achieved by encapsulation process or drying process.

A. Microencapsulation Process.

In some embodiments, the encapsulation of the disclosed microorganisms is done by extrusion technique (King A H et al., *Encapsulation and Controlled Release of Food Ingredients*, Sara J R and Gary A R, Eds., vol. 590 of *ACS Symposium Series*, 26-39, American Chemical Society, Washington, D.C., USA.). Extrusion method in the case of alginate capsule consists of the following stages: preparation of hydrocolloid solution and the addition of probiotic cell in hydrocolloid solution to form cell suspension. These cells suspension is passed through the syringe needle to form droplets which are directly dripped into the hardening solution containing cations like calcium. When the droplets come in contact with hardening solution, alginate polymers surround the core to form a three-dimensional lattice structure by cross-linking calcium ions (Kailasapathy K, *CAB Reviews*, 4(6) 1-19, (2009)), thereby entrapping the core material separated from liquid bath and is dried using a suitable technology. Formation of gel by alginate solution (0.6%) would be possible if calcium ion (0.3 M) is present. Usually, alginate is used in the range of 1-2% and 0.005-1.5 M calcium chloride concentration. Generally, the diameter of forming beads in this method (2-5 mm) is larger than those formed in the emulsion method. Bead diameter is affected by concentration and viscosity of alginate solution and distance between the syringe and hardening solution, and diameter of extruder orifice affects the size of bead. Bead diameter decreases along with increasing concentration and viscosity of the encapsulation solution. Using low glucuronic alginate, formation of beads with smaller diameter is possible (Smidsrod O et al., *Trends in Biotechnology*, 8(3):71-75 (1990)). For production of alginate capsule with Chitosan coat, alginate solution is dripped into the hardening batch containing calcium chloride and Chitosan. Soaking of alginate beads in the Chitosan solution (0.1%, pH 6.5) for 20 min gives rise to beads with good properties.

In some embodiments, the encapsulation of the disclosed microorganisms is carried out by emulsion technique, as demonstrated in the microencapsulation of lactic acid bacteria (Audet P et al., *Applied Microbiology and Biotechnology*, 29(1):11-18, (1988)). In this method, small volume of cell/polymer slurry (dispersed phase) is added to the large volume of vegetable oil (as a continuous phase) such as soy oil, sunflower, corn, and light paraffin oil. After the formation of emulsion, cross-linking is required to form gels. Gelification is done by different mechanisms like ionic, enzymatic, and interfacial polymerization as discussed next. It can be easily scaled up, and the diameter of producing beads is considerably smaller (25 μm-2 mm).

In some embodiments, the encapsulation of the disclosed microorganisms is done by emulsification and ionic gelification. Emulsification is a chemical technique to encapsulate probiotic using alginate, carrageenan and pectin as an encapsulating material. Once water in oil (W/O) emulsion is formed, water soluble polymer becomes insoluble after addition of ions of calcium chloride, by means of cross-linking forming gel particles in the oil phase. The smallest particle of the aqueous phase in W/O phase emulsion will lead to the formation of beads with smaller diameters. Agitation rate and type of emulsifier also affects the diameter of the beads. Microbeads produced by this technique are recovered by membrane filtration technology (Krasaekoopt W et al., *International Dairy Journal*, 13(1), 3-13, 2003).

In some embodiments, the encapsulation of the microorganisms is carried out by emulsification and enzymatic gelification. Milk protein is used to encapsulate probiotics by means of an enzyme-induced gelation (Heidebach T et al., *Food Hydrocolloids*, 23(7):1670-1677 (2009)). Milk proteins have excellent gelation properties and are a natural vehicle for probiotics. This method gives water insoluble and spherical particles. This method is an example of encapsulation by means of rennet gelation, which is based on the principle of using dairy proteins which have been put in contact with rennet at low temperature. This allows keeping a liquid system where κ-casein is cleaved by the enzyme. After that, dairy proteins are emulsified in a cold oil to form water in oil emulsion. Thermal induction of enzymatic coagulation allows protein flocculation and provides microparticles.

In some embodiments, the encapsulation of the disclosed microorganisms is carried out by emulsification and interfacial polymerization. This technique requires formation of an emulsion in which discontinuous phase contains an aqueous suspension of the cell and continuous phase contains organic solvent. To initiate the polymerization reaction, biocompatible agent which is soluble in the continuous phase is added. The drops of probiotic cell are coated to form thin and strong membrane (Kailasapathy K et al., *Current Issues in Intestinal Microbiology*, 3(2):39-48 (2002)).

In a preferred embodiment, the process of making the novel compositions is similar to the polymer capsule preparation using immobilized particles described by Richardson J J et al (Richardson J J et al., *Adv Mater.* 25(47):6874-8 (2013)).

B. Drying Process for Microencapsulation.

Drying improves stability of the encapsulated culture during prolonged storage. But the drying process causes some injuries to the microbeads, release of some cells, and reducing the viability of cells. Spray drying, freeze drying, and fluidized bed drying are used for the making of the current inventive compositions.

In some embodiments, the encapsulation of the disclosed microorganisms is carried out by spray drying. A solution containing probiotic living cells and the dissolved polymer matrix is prepared by using gum Arabic and starches because they tend to form a spherical microparticle during the drying process (de Vos P et al., *International Dairy Journal*, 20(4):292-302 (2010)). In drying process, probiotic cell loses viability due to physical injury to microencapsulate and heat generation. However, the loss of probiotic cell can be reduced by using proper cryoprotectant during freeze drying, optimizing the inlet and outlet temperature for spray drying (Champagene C P et al., *Functional Dairy Products*, 2:404-426 (2007)).

In some embodiments, the encapsulation of the disclosed microorganisms is carried out by freeze drying. In this technique, the solvent is frozen and removed via sublimation (Pikal M J, *PharmTech International*, 1:37-43 (1991)). Freezing causes damage to the cell membrane due to ice crystal formation and also imparts stress condition by high osmolarity. It has been traditionally used to stabilize probiotic bacteria, but the combination of freeze-drying and encapsulation is relatively new concept. Recently, *Lactobacillus* F19 and *Bifidobacterium* Bb12 cells were first encapsulated into enzymatically gelled sodium caseinate, and gel particles were freeze-dried to study the storage stability (Heideback T et al., *Journal of Food Engineering*, 98(3): 309-316 (2010)). They reported better post-drying survival and storage viability for encapsulated cell compared to free cell. In other recent work, gelatinized starch and lecithin were incorporated into the alginate microcapsule containing probiotic organisms in encapsulated form, and beads were freeze-dried to evaluate the storage stability at different temperature. It was shown that encapsulated bacteria had much better stability at 23° C. for 12 weeks, and lecithin helped in obtaining higher efficiency and more stability (Donthidi A R, et al., *Journal of Microencapsulation*, 27(1): 67-77, (2010)).

In some embodiments, the encapsulation of the disclosed microorganisms is carried out by fluidized bed drying. In this process, cell suspension is sprayed and dried on inert carriers using a Wurster-based fluidized bed system (Huyghebaert N et al. *European Journal of Pharmaceutics and Biopharmaceutics*, 61(3):134-141, (2005)).

In some embodiments, the encapsulation of the disclosed microorganisms is carried out by vacuum drying. Vacuum drying is suitable for heat sensitive probiotics because drying takes place at lower temperatures, and oxidation reaction can also be minimized, while disadvantage is batch operation and longer drying time which can be minimized by using a continuous vacuum dryer where cost is one-third of a freeze dryer, and the material can be dried at 1-4% moisture level at 40° C. within 5-10 min (Hayashi H et al., *Drying Technology*, 1(2):75-284, (1983)).

In some embodiments, spray freeze drying is sued to encapsulate. In this technique, the probiotic cell solution is atomized into a cold vapor phase of a cryogenic liquid such as liquid nitrogen, which generates a dispersion of frozen droplets. These are dried in freeze dryer (Kailasapathy K, *CAB Reviews*, 4(6) 1-19, (2009)).

In some embodiments, the following microencapsulation techniques are used for making the formulation: a microencapsulation technique known as Probiocap (US Patent Publication No. 20030109025). The process is based on coating freeze-dried Lactobacillus with fatty acids. This technology allows strains to resist the harsh effect of temperature, gastric acidity, and compression. Danish-Korean Company patented a duel coating technology for *Lactobacillus*, which is marketed under the brand name Duaolac®. The first layer of coating is made of soy peptide, and the second layer is made of cellulose and gum.

IV. Methods of Use

Methods of using the pH responsive, mucoadhesive microencapsulated microorganisms are provided.

A. Therapeutic and Prophylactic Administration

Pharmaceutical compositions for enhancing gut microbiota can be administered in a number of ways depending on the conditions to be treated. The methods for administering the disclosed compositions are essentially the same, whether for prevention or treatment.

In some embodiments, the disclosed compositions are included in dairy products such as yogurt, mayonnaise, cheese, kefir, cream and ice cream. In some embodiments, the disclosed compositions are included in products such as lactic acid, frozen dessert, tea, coffee, soda drinks, energy drink, breakfast cereal and snack bars, The composition can be administered during a period before, during, or after onset of disease symptoms, or any combination of periods before, during or after onset of one or more disease symptoms. For example, the subject can be administered one or more doses of the composition every 1, 2, 3, 4, 5, 6, 7, 14, 21, 28, 35, or 48 days prior to onset of disease symptoms. The subject can be administered one or more doses of the composition every 1, 2, 3, 4, 5, 6, 7, 14, 21, 28, 35, or 48 days after the onset of disease symptoms. In some embodiments, the multiple doses of the compositions are administered before an improvement in disease condition is evident. For example, in some embodiments, the subject receives 1, 2, 3, 4, 5, 6, 7, 14, 21, 28, 35, or 48, over a period of 1, 2, 3, 4, 5, 6 7, 14, 21, 28, 35, or 48 days or weeks before an improvement in the disease condition is evident.

The compositions can be administered alone, or in combination with a second active agent, as part of therapeutic regime for disease treatment. For example, the composition can be administered on the first, second, third, or fourth day, or combinations thereof. The composition can be administered on the same day, or a different day than the second active agent.

B. Microbiota-Associated Diseases and Conditions

Disease states may exhibit either the presence of a novel microbe(s), absence of a normal microbe(s), or an alteration in the proportion of microbes.

Work in recent years has implicated and described mechanistic explanations of how the microbiota is related to or causes specific disease states. Recent research has established that disruption of the normal equilibrium between a host and its microbiota, generally manifested as a microbial imbalance, is associated with, and may lead to, a number of conditions and diseases. These include Crohn's disease, ulcerative colitis, obesity, asthma, allergies, metabolic syndrome, diabetes, psoriasis, eczema, rosacea, atopic dermatitis, gastrointestinal reflux disease, cancers of the gastrointestinal tract, bacterial vaginosis, neurodevelopmental conditions such as autism spectrum disorders, and numerous infections, among others. For example, in Crohn's disease, concentrations of *Bacterioides, Eubacteria* and *Peptostreptococcus* are increased whereas *Bifidobacteria* numbers are reduced (Linskens et al., Scand J Gastroenterol Suppl. 2001; (234):29-40); in ulcerative colitis, the number of facultative anaerobes is increased. In these inflammatory bowel diseases, such microbial imbalances cause increased immune stimulation, and enhanced mucosal permeability (Sartor, Proc Natl Acad Sci USA. 2008 Oct. 28; 105(43):16413-4). In obese subjects, the relative proportion of *Bacteroidetes* has been shown to be decreased relative to lean people (Ley et al., Nature. 2006 Dec. 21; 444(7122):1022-3), and possible links of microbial imbalances with the development of diabetes have also been discussed (Cani et al., *Pathol Biol* (Paris). 2008 July; 56(5):305-9). Segmented Filamentous Bacteria have been shown to play a critical role in prevention of infection and development of autoimmune diseases (Ivanov et al, *Cell.* 139(3):485-98, 2009). In the skin, a role for the indigenous microbiota in health and disease has been suggested in both infectious and noninfectious diseases and disorders, such as atopic dermatitis, eczema, rosacea, psoriasis, and acne (Holland et al. 1977 Br J Dermatol. 96(6): 623-6; Thomsen et al. 1980 *Arch. Dermatol.* 116:1031-1034; Till et al. 2000 *Br. J. Dermatol.* 142:885-892; Paulino et al. 2006 *J. Clin. Microbiol.* 44:2933-2941). Furthermore, the resident microbiota may also become pathogenic in response to an impaired skin barrier (Roth and James 1988 *Annu. Rev. Microbiol.* 42:441-464). Bacterial vaginosis is caused by an imbalance of the naturally occurring vaginal microbiota. While the normal vaginal microbiota is dominated by *Lactobacillus*, in grade 2 (intermediate) bacterial vaginosis, *Gardnerella* and *Mobiluncus* spp. are also present, in addition to *Lactobacilli*. In grade 3 (bacterial vaginosis), *Gardnerella* and *Mobiluncus* spp. predominate, and *Lactobacilli* are few or absent (Hay et al., Br. Med. J., 308, 295-298, 1994)

Other conditions where a microbial link is suspected based on preliminary evidence include rheumatoid arthritis, multiple sclerosis, Parkinson's disease, Alzheimer's disease, muscular dystrophy, fibromyalgia and cystic fibrosis. Some evidence also suggests the link between commensal gut microbiota and the central nervous system. Bravo et al showed that ingestion of *Lactobacillus* strain regulates emotional behavior and central GABA receptor expression in a mouse via the vagus nerve (Bravo et al., *Proc Natl Acad Sci USA.* 108(38):16050-5(2011)). In some embodiments, the inhibition and treatment of the enteric pathogen diseases is accomplished by the probiotic composition through a competitive binding process.

Probiotic bacteria, *Lactobacillus fermentum* and *Bifidobacterium lactis*, appears to inhibit permeability caused by gliadin and therefore to reduce gliadin-induced cellular damage. Probiotic bacteria may reduce the damage caused by eating gluten-contaminated foods and may even accelerate mucosal healing after the initiation of a gluten-free diet (Lindfors K et al., *Clin Exp Immunol.* 152(3):552-8 (2008)). *Lactobacillus fermentum* and *Bifidobacterium lactis* are exemplary probiotic bacteria as a potential treatment for Celiac disease and gluten intolerance.

In some embodiments, the disclosed compositions are given to subjects with altered or non-optimal gut microbiota such as following a course of medical treatment that damages the healthy commensal microbiota. In some embodiments, the compositions are given to subjects following a course of antibiotic treatment. In some embodiments, the compositions are given to a subject following chemotherapy.

In some embodiments, the compositions are given to babies or children after a course of antibiotics for ear infections or yeast infections. In some embodiments, the compositions are given to premature babies for populating their gut commensal microbiome.

In some embodiments, the compositions are for transferring vaginal microbial communities to confer stability and resistance to bacterial vaginosis (BV). The microbial populations are preferably obtained from women with *Lactobacillus crispatus*-dominated (>50%) vaginal microbiota, who are healthy, free of sexually transmitted disease, and have a low pH in the secretions. The encapsulated microbial populations are administered to women with BV, as identified clinically with Amsel's criteria, and confirmed in the laboratory by Nugent scoring. Transplantation of more beneficial *lactobacillus* types, including the vaginal microbial community and the mucus environment in which they live, is a promising method for re-establishing healthy bacterial communities that do not compromise the structural and adhesive properties of cervicovaginal secretions in the vaginas of women with recurrent BV.

1. Intestinal Disorders

In some embodiments the disease or disorder that can be prevented or treated by the disclosed methods and compositions are intestinal diseases and disorders, such as gastroenteritis and irritable bowel syndrome (IBS). IBS is characterized by symptoms such as abdominal cramp, discomfort, bloating and inflammation of the colon, rectum, and/or the distal small intestine. Although the exact causes of IBS remains poorly understood, several of its pathologic features suggest that the disease derives in part from dysregulated control of bacterial interactions with the mucosal surface.

Other exemplary diseases and disorders of the GI tract include diarrhea, dysentery, cholera, hemorrhagic colitis, peptic ulcer disease, gastritis, and enteric fever (e.g., typhoid fever).

Exemplary invasive enteric bacteria strains that cause diseases and disorders of the GI tract include *Salmonella* spp (e.g., *S. choleraesuis, S. paratyphi A, S. schottmuelleri* and *S. hirschfeldii*), *Shigella* spp, *Campylobacter* spp. (e.g., *C. fetus, C. upsaliensis, C. lari, C. jejuni*), enterohepatic *Helicobacter* species (e.g., *H. cineadi, H. fennelliae*), *Vibrio* spp., *Clostridium* spp. (e.g., *C. difficile*), *Pseudomonas* spp., *Enterobacter* spp., *Arcobacter* spp., *Yersinia* spp., *Aeromonas* spp. and *Escherichia* spp.

Exemplary viruses that cause diseases and disorders of the GI tract include strains of adenoviruses, hepatitis E virus, astroviruses, noroviruses and other caliciviruses, reoviruses and rotaviruses.

C. Treating Conditions in Animals

The pH-responsive, mucoadhesive polymeric encapsulated compositions can also be administered to any animal in need of thereof including. Most common uses are in animals treated with antibiotics such as cats, dogs, horses and ruminants (sheep, cattle, goats, deer, llama) or newborns that did not get adequate colostrum and/or nurse their dams.

Specifically, the compositions e.g. containing probiotic, can be used to inhibit or treat enteric pathogen-associated diseases when administered to an animal in need thereof using the methods described in the present specification. Enteric pathogen diseases include those diseases caused by pathogens such as diarrhea, irritable bowel syndrome and intestinal hemorrhages. Examples of enteric pathogens associated with these diseases include, but not limited to enteropathogenic *Escherichia coli* (EPEC), enterotoxigeneic *E. coli* (ETEC), *Salmonella enteriditis, Yersina pseudotuberculosis* and *Listeria monocytogenes*. In some embodiments, the inhibition and treatment of the enteric pathogen diseases is accomplished by the probiotic composition through a competitive binding process. For example, the probiotic *lactobacilli* compete with enteric pathogens for binding sites on the intestinal mucosa. Because the probiotic *lactobacilli* have a higher affinity and avidity for these binding sites than the enteric pathogens, the probiotic *lactobacilli* displace the enteric pathogens into the intestinal milieu where they are harmlessly flushed from the intestines by normal metabolic processes. In vivo examples of this above described competitive binding and its efficacy in inhibiting and treating enteric pathogen diseases is provided in detailed examples below and in the accompanying figures.

D. Dosages and Effective Amounts

In some in vivo approaches, the compositions of encapsulated microorganisms are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease or disorder, and the treatment being effected, the number of times daily and number of days or weeks of treatment, and whether the probiotics are administered concurrently with antibiotics. The selected dosage depends upon the desired therapeutic effect, on the route of administration, and on the duration of the treatment desired.

Generally dosage levels are between 1-100 million colony forming units for human with a healthy digestive tract. For restoring microbiome after treatments that eliminate most gut microbiome for example, in case of antibiotic treatment or chemotherapy, the dosage level is about 1-100 billion colony forming units.

Preferably, the amount of encapsulated agents is effective to prevent or reduce the infection or onset of a disease or disorder in a subject compared to an untreated control.

In another embodiment, the encapsulated agents are in an amount effective to promote and encourage healthy commensal microbiota and decrease the amount of inflammation, pain or other symptoms associated with a disease or disorder in a subject.

In a preferred embodiment the effective amount of encapsulated agents does not induce significant cytotoxicity in the GI tract of a subject compared to an untreated control subject.

In some embodiments, the dosage levels for dogs and cats are about 500 million to 50 billion CFUs; for horses and cattle are about 1 billion to 100 billion CFUs.

In one embodiment, an animal is provided with a single dose containing from approximately $10^5$ to $10^{11}$ CFU of probiotic bacteria e.g. *lactobacilli* per gram of probiotic composition. The total amount consumed will depend on the individual needs of the animal and the weight and size of the animal. The preferred dosage for any given application can be easily determined by titration. Titration is accomplished by preparing a series of standard weight doses each containing from approximately $10^5$ to $10^{11}$ *lactobacilli* per gram. A series of doses are administered beginning at 0.5 grams and continuing up to a logical endpoint determined by the size of the animal and the dose form. The appropriate dose is reached when the minimal amount of *lactobacilli* composition required to achieve the desired results is administered. The appropriate dose is also known to those skilled in the art as an "effective amount" of the pH-responsive, mucoadhesive polymeric encapsulated compositions.

For example, if it is desired to reduce the symptoms associated with irritable bowel syndrome in an animal, one measured dose as described above is administered daily, escalating the dose each successive day in 0.5 grams increments until symptoms subside. In one embodiment the preferred dose is between approximately $10^3$ to $10^8$ viable *lactobacilli* per kilogram of body weight (the weight of animal recipient) per day. This equates to approximately 10 billion viable *Lactobacillus casei* strain KE01 per day for the average healthy adult human. By extrapolation, it is a simple matter to calculate the approximate dose appropriate for any animal of any weight. It is understood that this is a non-limiting example that can be varied as appropriate by persons having skill in the art of prescribing probiotic compositions or by using the titration method provided above.

E. Controls

The effect of pH-responsive, mucoadhesive polymeric encapsulated agent can be compared to a control. Suitable controls are known in the art and include, for example, an untreated subject. In some embodiments, the control is untreated tissue from the subject that is treated, or from an untreated subject. In some embodiments, an untreated control subject suffers from, or is at risk from the same disease or condition as the treated subject e.g. Crohn's disease.

F. Combination Therapy

The disclosed methods and compositions for delivering encapsulated agent can be administered alone, or in combination with one or more additional active agent(s), as part of a therapeutic or prophylactic treatment regime. The pH-responsive, mucoadhesive polymeric encapsulated agent can be administered on the same day, or a different day than the second active agent. For example, compositions including encapsulated agents can be administered on the first, second, third, or fourth day, or combinations thereof.

The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second). The additional therapeutic agents can be administered locally or systemically to the subject, or coated or incorporated onto, or into a device.

In some embodiments, the additional agent or agents can modulate the local gut environment. In some embodiments, the additional agent can act systemically in the host such as for relieving signs and symptoms related to the disease and conditions to be treated. Some non-limiting examples include anti-diarrheal medications, pain relievers, iron supplements, vitamin B-12 shots, calcium and vitamin D supplements and other supplemental nutrition given as enteral nutrition or parenteral nutrition.

In some embodiments, the additional agent could be anti-inflammatory drugs such as aminosalicylates and corticosteroids. In some embodiments, the additional agent could be immune suppressors such as azathioprine (Azasan, Imuran), mercaptopurine (Purinethol, Purixan), cyclosporine (Gengraf, Neoral, Sandimmune), infliximab (Remicade), adalimumab (Humira), golimumab (Simponi), methotrexate (Rheumatrex), natalizumab (Tysabri), vedolizumab (Entyvio) and Ustekinumab (Stelara). In some embodiments, the additional agent could be antibiotics such as Metronidazole (Flagyl) and Ciprofloxacin (Cipro).

The present invention will be further understood by reference to the following non-limiting examples.

EXAMPLES

Example 1: Layer-by-Layer Templating of *Bacillus coagulans*

Methods and Materials

Bacteria Growth

*Bacillus coagulans* (ATCC #7050) ("BC") were grown at 37 C in Difco nutrient broth and on Difco nutrient agar (VWR) and used for all experiments and stored while in the exponential phase. Counting of bacteria was performed using the standard plate counting method streaked with glass beads, where all plates had between 30-100 colonies. Prior to plating, all formulations were first resuspended and washed twice in PBS. For IVIS experiments, bacteria were stained with vivotag-S 750 (20 µl of a 10 mg/ml vivotag-S 750 in DMSO in 5 mg of bacteria in 980 µl of pH 8.5 210 mM bicarbonate buffer) under rotation at room temperature for 1 hour.

BC, either plain or encapsulated, were grown under shaking conditions (225 RPM) at 37° C. using an INNOVA® 44 incubating shaker. OD600 readings were obtained using a SPECTRAMAX® Plus 384 spectrophotometer with media-only backgrounds subtracted. In the case of pH-responsive growth, media was adjusted to be pH 4.5 for acidic conditions and used as made (pH 7.1) for neutral conditions.

For IVIS experiments, bacteria were fluorescently labeled with VIVOTAG-S® 750 (20 µl of a 10 mg/ml VIVOTAG-S® 750 in DMSO with 5 mg of BC in 980 µl of pH 8.5 210 mM bicarbonate buffer) under rotation at room temperature for 1 hour.

Transformation of BC with pGEN-luxCDABE (Lane et al., *Proceedings of the National Academy of Sciences*, 104: 16669-74 (2007)) was performed following a standard heat-shock protocol. Briefly, 150 µl of bacteria were incubated on ice with 5 ng of pure plasmid DNA for 30 minutes, heat-shocked for 45 seconds at 42° C., and placed back on ice for 2 minutes. 800 µl of SOC medium was added to the tubes and incubated for 1 hour at 37° C. 50 µl of this suspension was plated on LB agar plates with ampicillin and incubated over night at 37° C. Individual colonies were selected, and luminescence was verified using IVIS imaging.

Layer-by-Layer Synthesis

Glycol chitosan and alginate (Sigma) were prepared as 2 mg/ml solutions in 0.5 M NaCl. EPO and L100 were prepared at 2 mg/ml in 0.5 M NaCl. The pH of chitosan and alginate solutions was 6.0 and 1 molar HCl and/or 1 molar NaOH were used to adjust pH as needed. EPO and L100 were prepared in 0.5 M NaCl by first dissolving EPO in pH 2 NaCl and L100 in pH 9 NaCl and titrating to a final pH of 6.0 NaCl for each. 5 mg/ml of bacteria were first suspended in 0.5 M NaCl and washed twice. Cationic polymers (e.g. EPO or chitosan) were first layered on plain bacteria using 1 ml of 2 mg/ml polymer solution as described above, for 30 minutes at room temperature. Bacteria were then washed 2× in 0.5 M NaCl and then coated identically with anionic polymers (e.g. L100 or alginate) for 30 minutes at room temperature. This process was repeated as necessary to synthesize LbL-probiotics of up to 3 bilayers (6 total layers).

Characterization of Layers

A Malvern zeta sizer was used to measure zeta potentials in either pH 1 or pH 7 pure water. Fluorescent chitosan and alginate polymers (PEGWorks) were coated identically to methods described above. A Tecan plate reader was used to measure fluorescent signals of the supernatant or templated probiotics in PBS, SIF, or SGF. A Carl Zeiss Axiovert 200M was used for taking brightfield images of probiotics and LbL-probiotics.

Results

FIG. 1 illustrates a schematic presentation of Layer-by-Layer (LbL) templating of individual bacteria. For example, a probiotic strain such as Bacillus coagulans can be templated with different polyelectrolytes, including polysaccharides chitosan, alginate and enteric pH responsive polymers such as EUDRAGIT® EPO and L100.

Figure 2A:
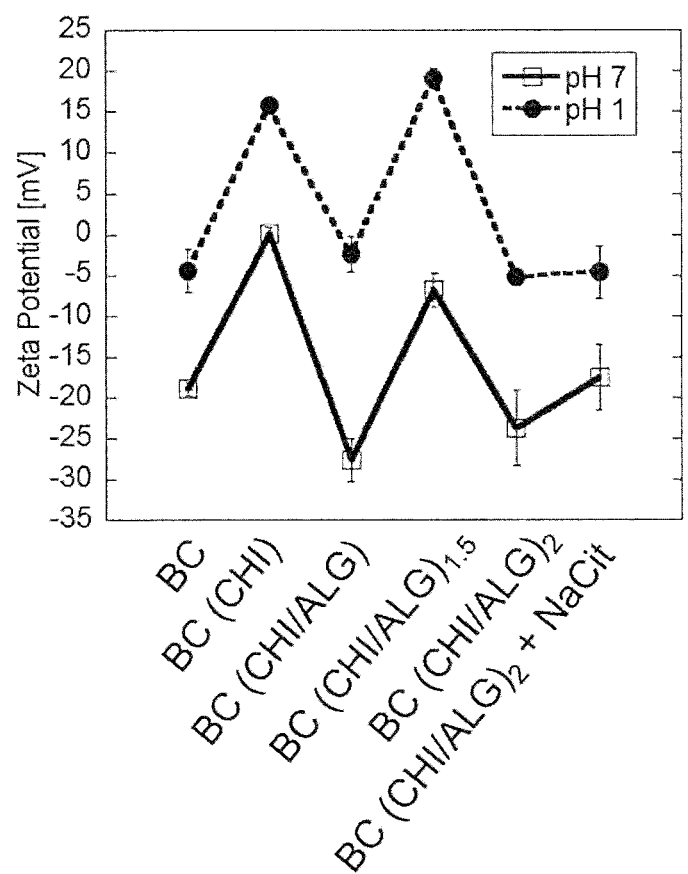
FIGS. 2A-2B are line diagrams showing layer characterization for chitosan (CHI) and alginate (ALG) coatings on model probiotic organism *Bacillus coagulans* (BC).

Layer characterization for chitosan (CHI) and alginate (ALG) coatings on model probiotic Bacillus coagulans (BC) was carried out by measuring the zeta potential (FIG. 2A). Zeta potential was measured for each sequential layer of coating, up to two bilayers of chitosan and alginate, (CHI/ALG)$_2$, at pH 1 and 7

Figure 2B:
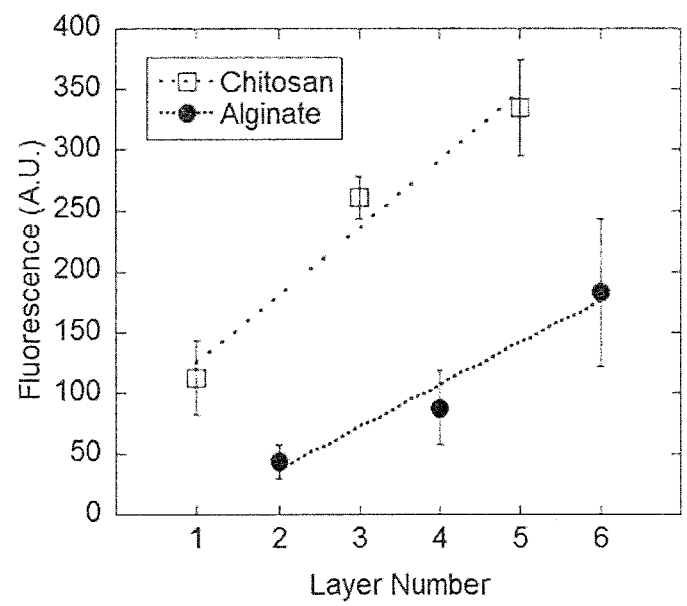

Uniform layer templating for up to 3 bilayers of chitosan and alginate was confirmed using fluorescent chitosan and alginate (FIG. 2B). Linear increases in fluorescent intensity imply uniform layer buildup for both polysaccharides.

Bright field imaging revealed that LbL-templating was achieved on single cells although the LbL-probiotics tend to aggregate once coated with 2 bilayers of chitosan and alginate (CHI/ALG)$_2$ (data not shown).

Example 2: Layer Stability in Simulated Intestinal Fluid and Simulated Gastric Fluid Methods and Materials As described in Example 1.

Figure 3A:
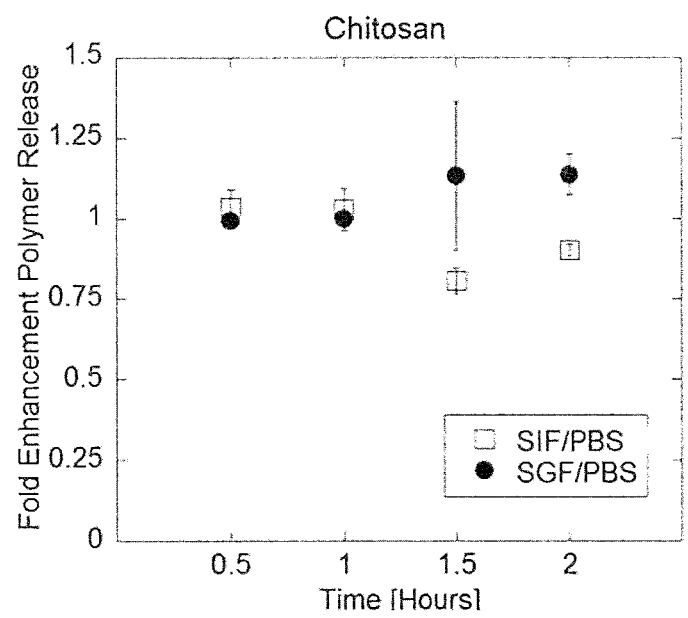
FIGS. 3A-3B are graphs showing fold enhancement of polymer release from 2-bilayer templating on *Bacillus coagulans* over time (hours) in either simulated intestinal fluid (SIF/PBS) or simulated gastric fluid (SGF/PBS) relative to their release in PBS.
Figure 3B:
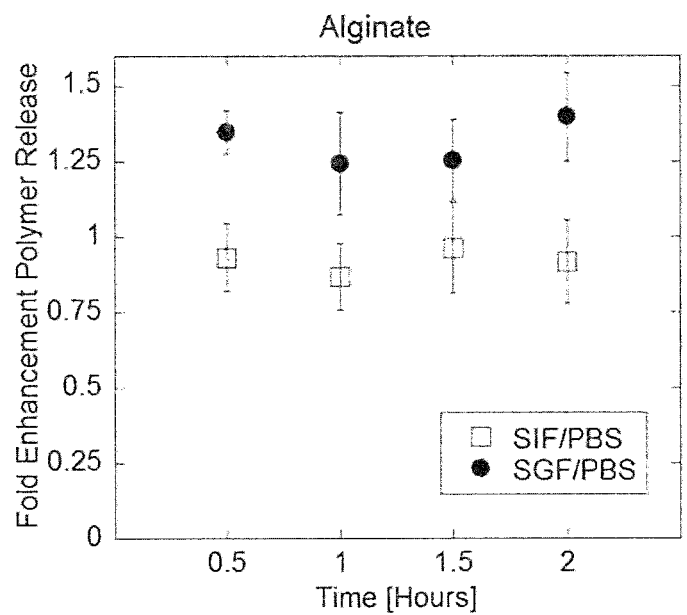

Results 2-bilayer of chitosan and alginate templated on Bacillus coagulans remained stable under physiologically relevant conditions (FIGS. 3A and 3B). This result suggests that layers will not be readily removed or destroyed due to conditions typically encountered in the GI tract.

Example 3: Layer-by-Layer Templating Protects Encapsulated Probiotics Against Biological Insults Methods and Materials Probiotic Response to Insults Plain or LbL-coated Bacillus coagulans were subjected to either 4% bile salt solution (Sigma) or SGF (Bicca) in a water bath at 37 C for up to 2 hours. After 2 hours, bacteria were pelleted at 3000 g and resuspended and washed twice in PBS. Bacteria were plated in sequential dilutions of ten and allowed to grow for at least 48 hours at 37 C, and counted as described in Example 1.

Results

Figure 4A:
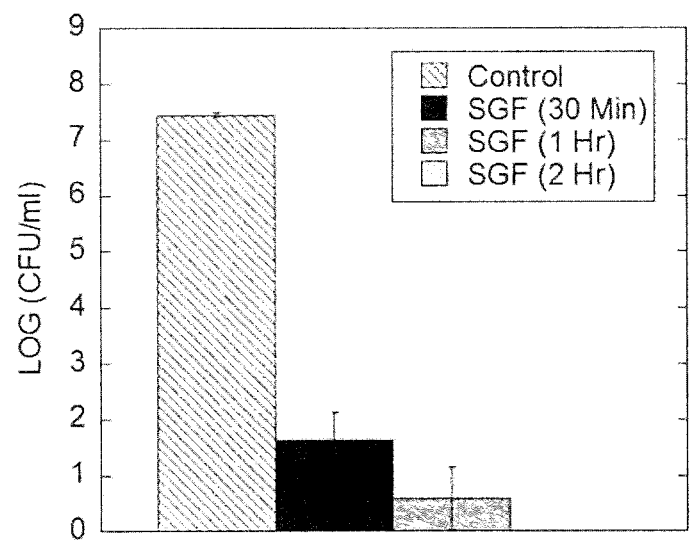
FIGS. 4A-4C are bar graphs showing the survival rate of non-formulated *Bacillus coagulans* (plain) and Layer-by-Layer (LbL) coated *Bacillus coagulans* under simulated gastric fluid (SGF) insult or bile insult at 37° C. over time of hours. The survival rate is measured in colony forming unit per ml of culture (CFU/ml).
Figure 4B:
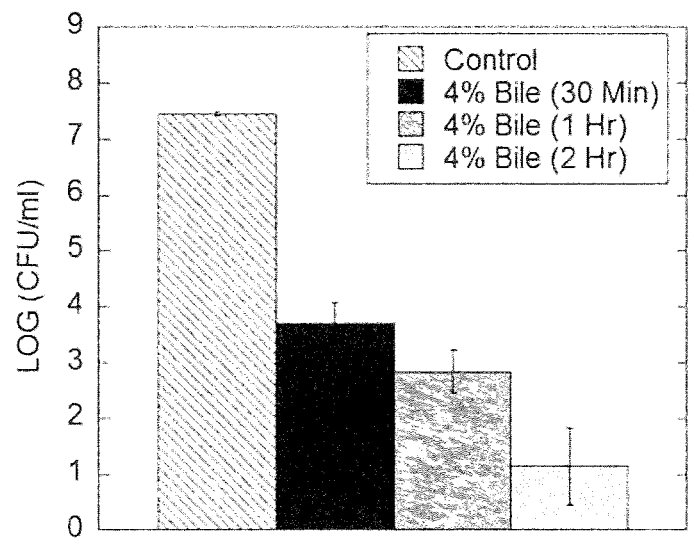
Figure 4C:
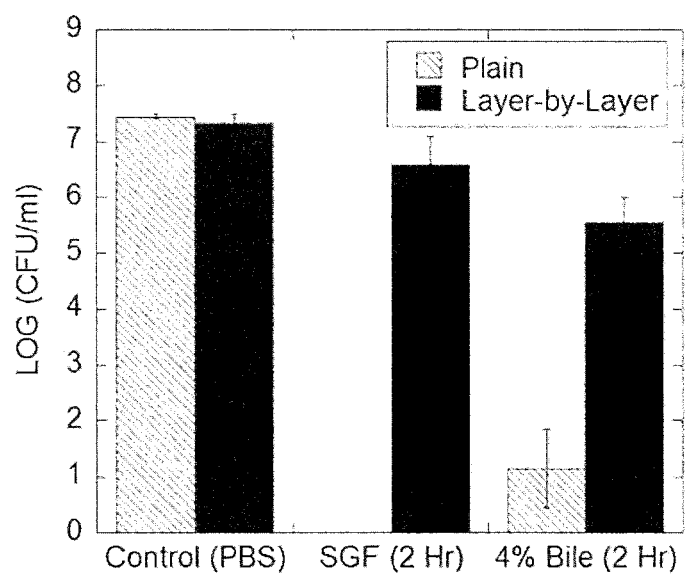

LbL-probiotics resisted acid and bile salt insults. Non-modified Bacillus coagulans exhibited rapid decrease in viability (colony forming units) in both simulated gastric fluid (SGF) and 4% bile salts (FIGS. 4A-4B). 2-bilayers of chitosan and alginate protected against biological insults. LbL-coating of (CHI/ALG)$_2$ provided protection to Bacillus coagulans against SGF and bile salts (FIG. 4C). LbL-formulated (CHI/ALG)$_2$ Bacillus coagulans were protected against both acidic and bile salt insults at 37 C for at least 2 hours.

FIG. 4C shows the sequential LbL coating of cationic chitosan and anionic alginate on a model gram positive probiotic, Bacillus coagulans, facilitated over 6 orders of magnitude increase in survival in simulated gastric fluid and over 5 orders of magnitude increase in survival in bile salts, as compared to uncoated, non-layered Bacillus coagulans.

Example 4: Layer-by-Layer Enhances Mucoadhesive Capabilities of Encapsulated Probiotics Methods and Materials Mucoadhesive Assay Freshly isolated small intestine from porcine were cleaned and sectioned. 100 µl of a 5 mg/ml solution of vivotag-S 750 stained probiotics, including plain, chitosan coated, and (CHI/ALG)$_2$ formulations, were pipetted directly onto the inner wall of the small intestines. Samples were then incubated for 1 hour at 37 C before immediately imaged using an IVIS Spectrum-bioluminescent and fluorescent imaging system (Xenogen). Analysis and spectral unmixing was performed using Living Image Software (PerkinElmer).

Results

Figure 5:
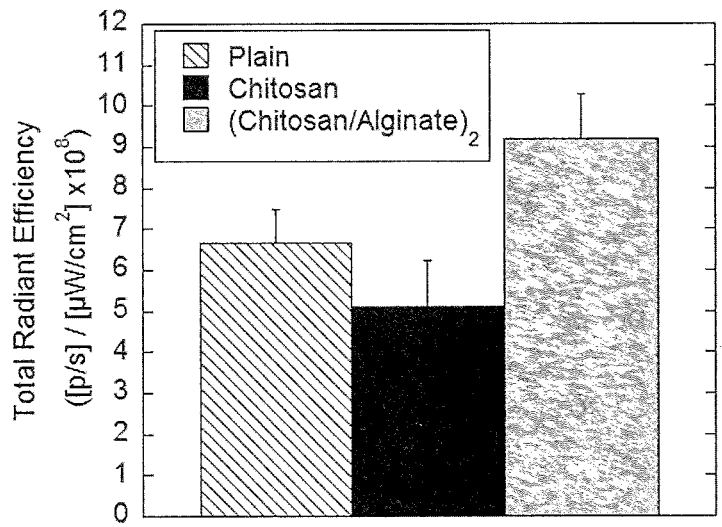
FIG. 5 is a bar graph showing mucoadhesive capabilities (measured in total radiant efficiency) of non-formulated *Bacillus coagulans* (plain), chitosan coated *Bacillus coagulans* (Chitosan) and 2-bilayers of chitosan and alginate coated *Bacillus coagulans* (Chitosan/Alginate)$_2$.

Mucoadhesive LbL coating of (CHI/ALG)$_2$ provided a 1.5-fold enhancement in mucoadhesion to ex vivo pig small intestine (FIG. 5A). The 2-bilayer coating clearly enhanced mucoadhesive capabilities over non-formulated bacteria.

Example 5: pH-Responsive Layer Removal

Methods and Materials pH-Responsive Layer Removal

Enteric polymer (EPO or L100) coated probiotics were subjected to pH treatments using either SGF or SIF for 1 hour at 37° C. Zeta potential measurements were taken at each layer coating and also following pH treatment.

Results

Figure 6A:
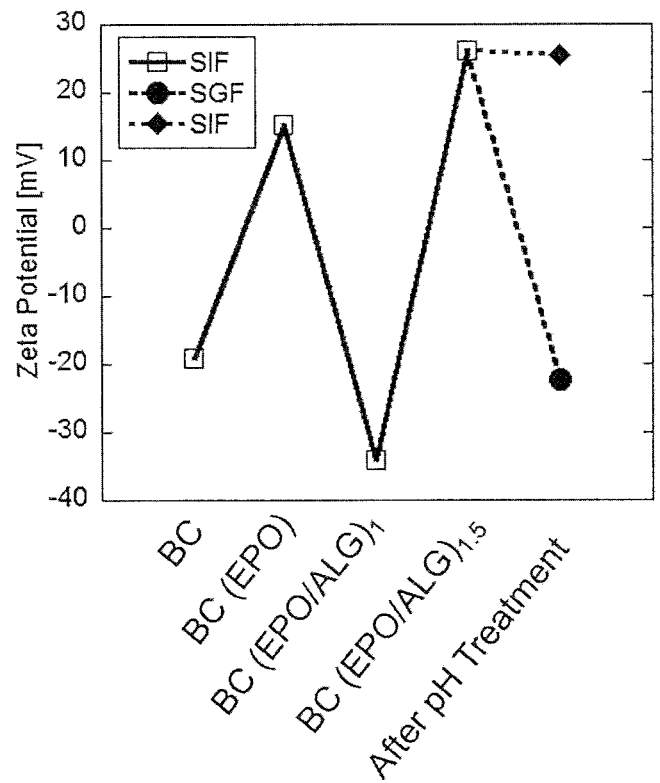
FIGS. 6A-6B are line graphs showing layer characterization for enteric pH-responsive polymers EUDRAGIT® EPO (EPO) and EUDRAGIT® L100 coatings onto the probiotic *Bacillus coagulans*.
Figure 6B:
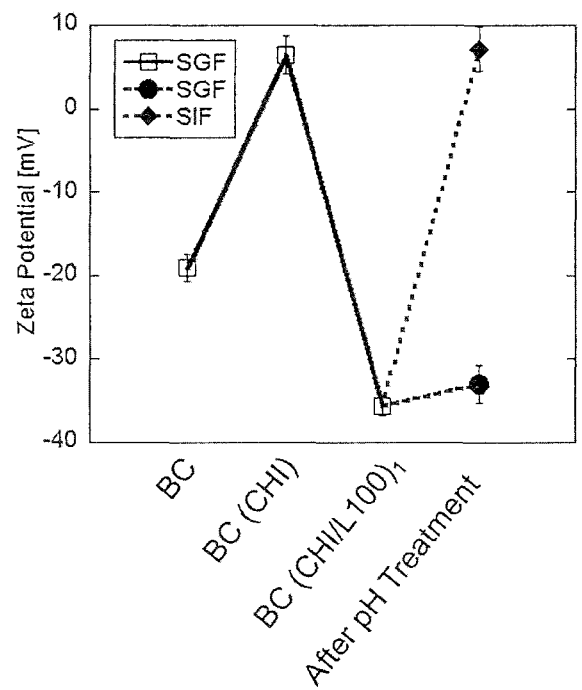

LbL-probiotics were constructed from enteric and FDA-approved pH responsive polymers such as EUDRAGIT® EPO for stimuli-responsive layer removal in specific areas of the GI tract (FIGS. 6A and 6B). When EPO was included as the terminal layer, exposure to acidic solutions facilitated removal of EPO, whereas continued exposure to neutral conditions did not. When EUDRAGIT® L100 was included as the terminal layer, exposure to neutral solutions facilitated removal of L100, whereas continued exposure to acidic conditions did not.

This proof-of-principle example illustrates that LbL-probiotics can be constructed from pH-responsive polymers for stimuli-responsive layer removal in specific areas of the GI tract. pH-responsive layer release can be integrated into LbL-probiotics via terminal coatings of enteric EPO and L100 EUDRAGIT® polymers. This offers a general approach to ensure stability and survival of bacteria/probiotics through the stomach for pH-mediated delivery and growth at the intestines or colon.

In summary, a layer-by-layer (LbL) method for the single encapsulation of bacteria cells to directly modulate the microbiome can be achieved by: (i) protecting LbL-bacteria from harsh stomach conditions to circumvent acid- or bile salt-mediated bacteria death, (ii) facilitating mucoadhesion via inclusion of mucoadhesive polysaccharides (e.g. chitosan) in the terminal layer, and (iii) controlling layer release via pH sensitive polymers so as to facilitate growth in pH-regulated areas of GI tract.

Example 6: Number of Bilayer Modulates Bacterial Growth

Figure 7:
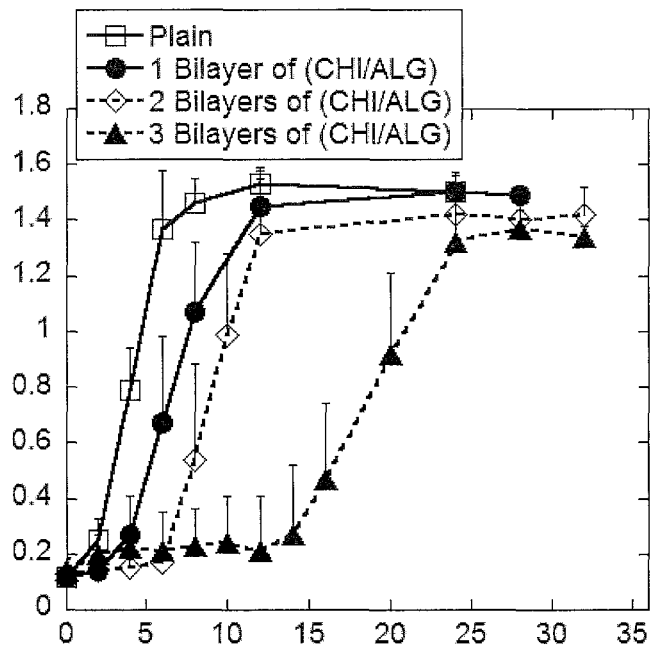
FIG. 7 is a line graph showing growth of bacteria with 0, 1, 2, or 3 bilayers of coating over time (hours) estimated by the absorbance at 600 nm (OD 600). (CHI/ALG), (CHI/ALG)$_2$, and (CHI/ALG)$_3$ on *Bacillus coagulans*, was used as the layer formulation for 1, 2 and 3 bilayers, respectively. Plain was used to describe 0-bilayer *Bacillus coagulans*.

Methods and Materials
As described in Example 1.
Results
FIG. 7 shows that as bilayer number increased from 0 to 3, growth rates of bacteria reduced accordingly. Therefore, the layer of bilayers can be designed as a way to modulate bacterial growth.

In summary, the above examples showed that LbL templating can be used to protect probiotics from harsh stomach conditions, to directly facilitate mucoadhesion and control layer release via pH sensitive polymers. Furthermore, LbL templating can be used as a way to control rate and overall growth of bacteria. This technology offers a platform based approach to ensure stability and survival of probiotics through the stomach for pH-mediated delivery to, and growth in the intestines and colon.

Figure 8:
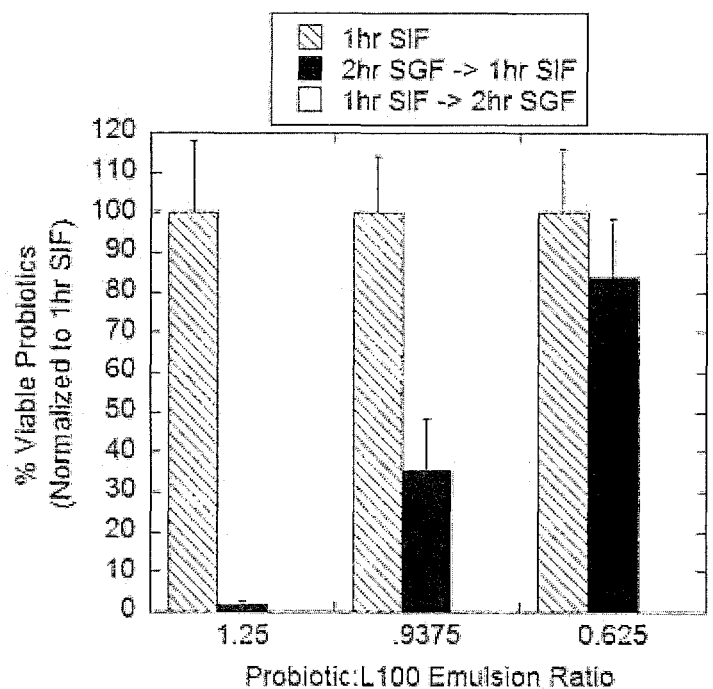
FIG. 8 is a bar graph showing viability of model probiotics *Bacillus coagulans* (BC) at different probiotic to EUDRAGIT® L100 emulsion ratio. Hatched bars show EUDRAGIT® L100 microencapsulated BC exposed directly to simulated intestinal fluid (SIF) and then plate counted. Black bars show the same mass of particles first exposed to acidic simulated gastric fluid (SGF) and then to neutral SIF. White bars show the same mass of particles first exposed to neutral SIF, followed by exposure to acidic SGF.

Example 7: pH-Responsive Polymeric Encapsulation of Multiple Probiotic Bacteria Methods and Materials
As described in Example 1.
Results
PH-responsive polymers such as EUDRAGIT® L100 can be used to encapsulate multiple bacteria within the same polymeric particle. In FIG. 8, the probiotic bacteria *Bacillus coagulans* (BC) were encapsulated in L100 at various probiotics:polymers ratios. Encapsulations with L100 lead to enhancement of probiotic survival following acidic insults. Subsequent exposure to neutral SIF conditions, under which the encapsulating L100 polymers dissolve, gave rise to a significant enhancement in the survival of encapsulated BC after acidic insults. In contrast, BC could not survive acidic conditions when the same mass of BC was first exposed to neutral SIF, followed by exposure to acidic SGF.

In addition, higher L100 polymer content resulted in probiotics with further enhanced viability after acidic insults. This suggests a better protection through acidic insults can be achieved with increased amount of coating polymers.

The example demonstrates that the same polymer coating technique is applicable to encapsulate multiple microorganisms to be delivered to specific sites within the GI tract.

Figure 9A:
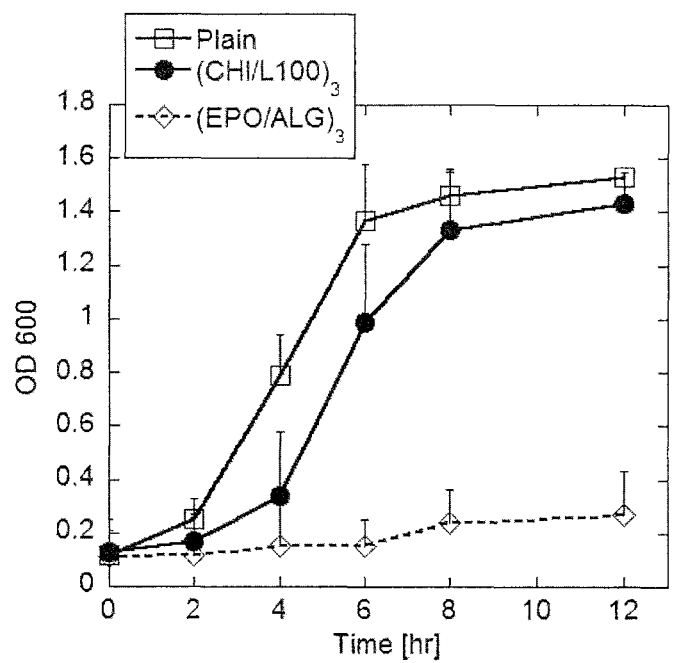
FIGS. 9A and 9B are line graphs showing the growth (measured in OD 600) of unencapsulated bacterial cells ("BC") (plain, open squares), pH-responsive polymer encapsulated BC with L100 as the terminal layer ((CHI/L100)$_3$, closed circles), and pH-responsive polymer encapsulated BC with EPO is the terminal layer ((EPO/ALG)$_3$, open diamonds) over time (hours) in neutral pH 7 (FIG. 9A) and acidic pH (FIG. 9B).
Figure 9B:
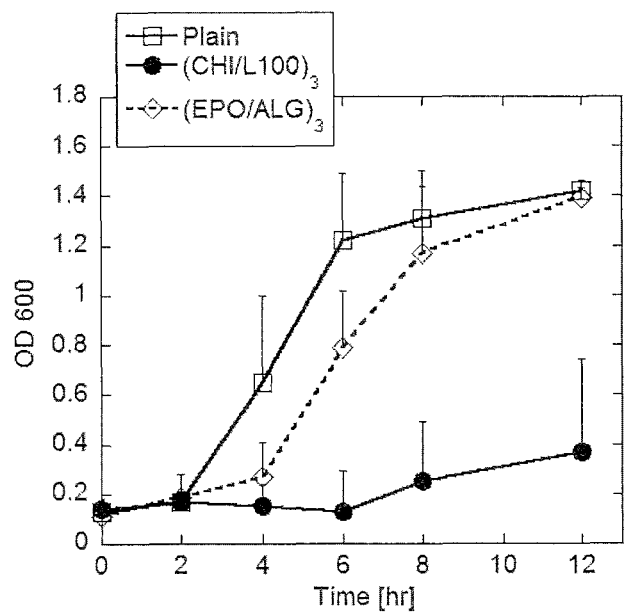

Example 8: pH-Responsive Polymeric Encapsulation of Probiotic Bacteria Affects Bacterial Growth in Conditions with Neutral or Acidic pH Methods and Materials
As described in Example 1
Results
FIGS. 9A and 9B demonstrate the growth rate of the LbL-probiotics grown at different pH conditions. When L100 is the terminal layer (closed circles), exposure to neutral conditions facilitates bacteria growth; however, when EPO is the terminal layer (open diamonds), exposure to neutral conditions prevents bacteria growth (FIG. 9A). When EPO is the terminal layer (open diamonds), exposure to acidic conditions facilitates bacteria growth; however, when L100 is the terminal layer (closed circles), exposure to acidic conditions prevents bacteria growth (FIG. 9B).

This data demonstrates that LbL-probiotics constructed from enteric and FDA-approved pH-responsive polymers can be selectively grown in different pH conditions.

Figure 10A:
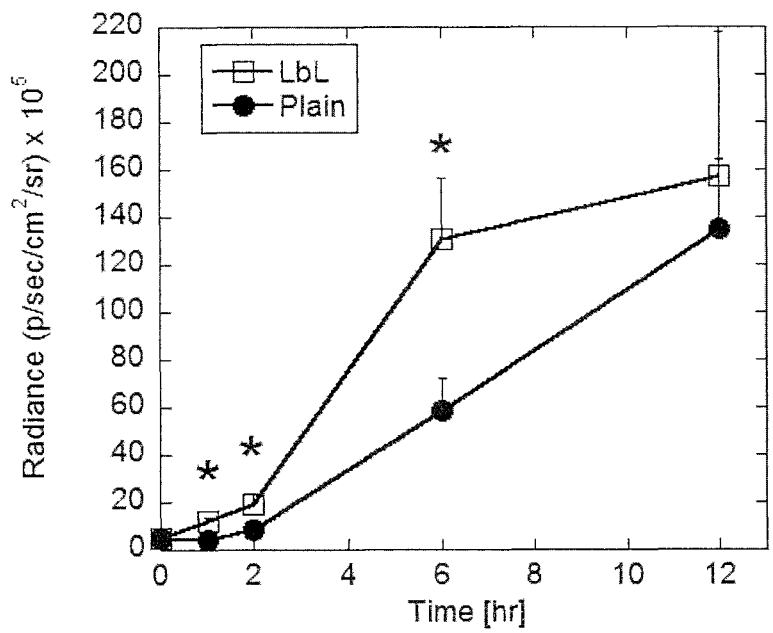
FIG. 10A is a line graph showing the growth rate (measured in Radiance (p/sec/cm$^2$/sr)×10$^5$) of plain, uncoated, bacteria (closed circles) and (CHI/ALG)$_2$-coated LbL-probiotics over time (hours) in EpiIntestinal® 3D tissue model at 37° C. (* p<0.05).
Figure 10B:
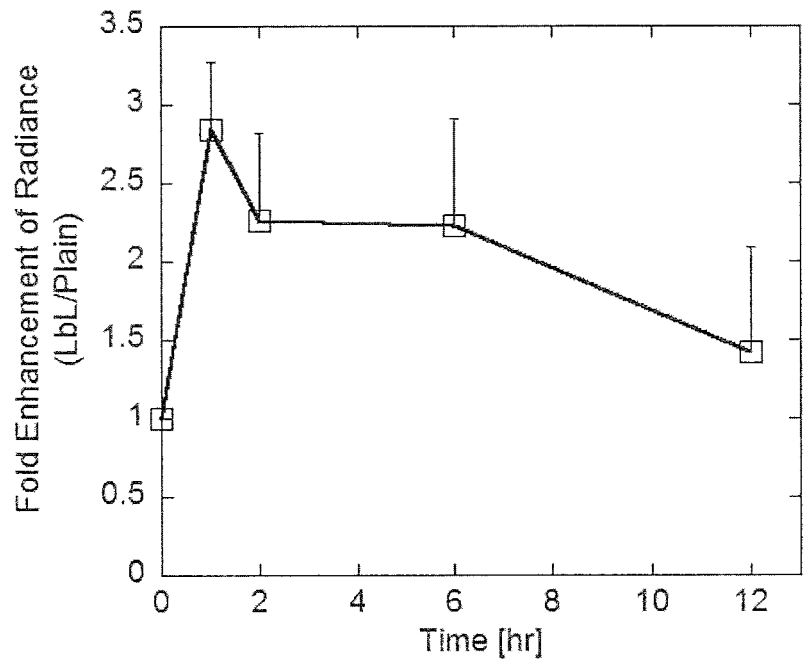
FIG. 10B is a line graph showing the fold-enhancement of LbL-probiotics' growth over that of plain, uncoated, probiotics at each time point.

Example 9: LbL Coating Significantly Enhances Probiotic Bacterial Growth in a Three-Dimensional Intestinal Tissue Model Methods and Materials
EpiIntestinal™ tissues were purchased from MatTek and used as recommended under antibiotic free conditions. For growth experiments, $1 \times 10^7$ BC were applied to the apical side of the EpiIntestinal tissue (n=3 per group) in 50% nutrient broth and 50% maintenance medium (MatTek). After 1 hour of incubation at 37° C. and 5% $CO_2$, non-adhered BC were washed 3× using sterile PBS. IVIS images of MatTek tissues with BC were taken at specific time points. TEM, confocal, and histology images were provided by MatTek.
Results
Intestine-mimicking tissues from humans (MatTek EpiIntestinal) were used to compare the growth of plain and LbL-probiotics on live mammalian intestine tissues. The EpiIntestinal™ system is an intestinal model proven to recreate physiological intestine structures (Jirova et al., *International Conference on Chemical, Civil and Environmental Engineering*, June 5-6: 66-68 (2015)) such as the columnar growth of intestinal epithelial cells, tight junctions, and brush borders (images taken but not shown). Bioluminescent plain and $(CHI/ALG)_2$ LbL-probiotics were placed in direct contact with EpiIntestinal™ tissue for 1 hour, washed, imaged, and analyzed for total emitted radiance to track and compare their adhesion and growth kinetics (FIG. 10A, 10B). Since unbound BC would pass through the GI tract in physiological situations, unbound BC were washed from the EpiIntestinal™ surface at each timepoint. At 1, 2, and 6 hours, adherence and growth of $(CHI/ALG)_2$ LbL-probiotics outperformed plain-probiotics, sometimes by as much as 2-fold (6 hours) (FIG. 10A, 10B). However, at 12 hours, these differences diminished as the intestinal surface begun to saturate.

The LbL-probiotic bacteria showed significantly faster growth at 1, 2, and 6 hours after plating when compared to the growth of plain bacteria (FIG. 10A). Fold-enhancement of LbL-probiotics' growth over that of plain, uncoated, probiotics at each timepoint is shown in FIG. 10B. The LbL coating enhanced the growth rate of $(CHI/ALG)_2$-coated LbL-probiotics by more than two-fold at these time points.

Histology (hematoxylin and eosin stain) of EPIINTESTINAL™ tissue highlighted the columnar growth of intestinal cells at 50× magnification. TEM imaging of EPIINTESTINAL™ tissue highlighted the presence of tight junctions and brush borders at 12,000×. Confocal imaging of EPIINTESTINAL™ tissue highlighted the presence of brush borders and columnar epithelium.

Example 10: LbL Coating Significantly Enhances Probiotic Bacterial Delivery to the to the GI Tract Methods and Materials
8-10 week old female BALB/c mice were oral gavaged $5 \times 10^8$ plain or LbL *Bacillus coagulans* (n=4 mice per group). After 1 hour, mice were sacrificed via $CO_2$ overdose and the GI tract (stomach to colon) was harvested. The GI tract was then opened with a razor blade to expose the gavaged BC to oxygen for bioluminescent imaging. All animal procedures were performed according to MIT Animal Care and Use Committee approved protocols.

Results

Figure 11A:
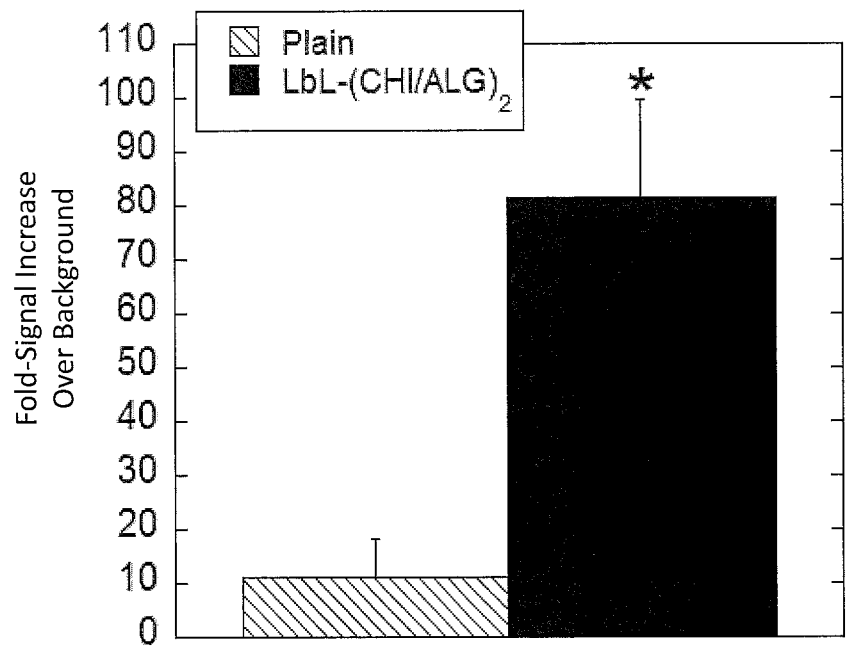
FIG. 11A is a bar graph showing fold signal increase over background of bioluminescent plain (hatched bar) and LbL-(CHI/ALG)$_2$-encapsulated (black bar) BC bound to mouse GI tract. Fold-signal increase between plain and LbL Bc 1 hour after oral gavage of an identical number of BC showed statistical difference. Error bars represent standard deviation (n=4), (*P<0.05) using Student's t-test between plain and LbL groups.

The role of LbL coatings on survival and delivery of probiotics in vivo was investigated by orally gavaging an identical number of bioluminescent plain and (CHI/ALG)$_2$ LbL-probiotics. 1 hour after oral gavage, bioluminescent (CHI/ALG)$_2$ LbL-probiotics emitted over 5-fold enhanced signal over background in the GI tract as compared to plain-probiotics (FIG. 11A). Representative images (not shown) highlighted how the GI tract distribution between plain-probiotics and (CHI/ALG)$_2$ LbL-probiotics were similar; however, unlike plain-probiotics, (CHI/ALG)$_2$ LbL-probiotics were capable of surviving harsh stomach conditions to arrive at the intestine in a viable state.

Figure 11B:
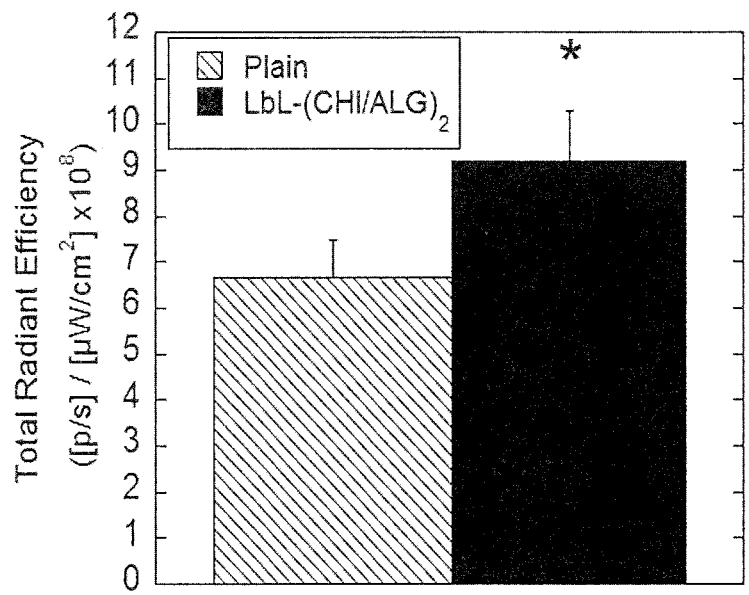
FIG. 11B is a bar graph showing total radiant efficiency as measured by IVIS of plain (hatched) and LbL (black) BC at 1 hour following mucoadhesion to pig intestine. Error bars represent standard deviation (n=3). * denotes statistical difference (P<0.05) using Student's t-test between plain and LbL groups.
Figure 12:
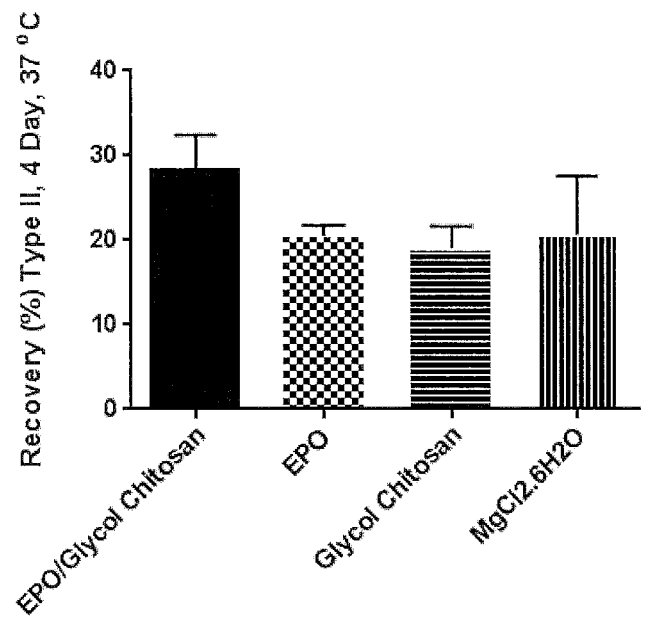
FIG. 12 is a bar graph showing the recovery of Type II oral poliovirus (OPV) after 4 days at 37° C. when encapsulated in a single layer of EPO, a single layer of Glycol Chitosan, or a single layer of 50:50 mixture of EPO and glycol chitosan compared to a standard salt buffer of MgCl$_2$.6H$_2$O.

The impact of LbL-coatings on probiotic mucoadhesion and growth on intestinal tissues was investigated using freshly isolated pig intestines and intestine-mimicking tissues from humans. After 1 hour incubation at 37° C. and subsequent washes, (CHI/ALG)$_2$ LbL-probiotics adhered to the mucosal surface of freshly isolated pig intestine nearly 1.5-fold higher as compared to plain-probiotics (FIG. 11B). LbL coatings enhanced mucoadhesion to pig intestine at 1 hour.

Collectively, these results demonstrate that the enhanced mucoadhesion provided by LbL-probiotics leads to growth advantages at later timepoints. Since more bacteria adhere directly to the intestine tissue at short timepoints, they replicate and reach the exponential growth phase faster. In vivo, LbL probiotics outperformed plain probiotics in terms of survival (FIG. 11A), likely due to an interplay occurring between resistance against acid/bile salts, intestinal adhesion, and subsequent growth.

Example 11: Encapsulation of Type II Oral Poliovirus

Methods and Materials

As described in Example 1.

Results

In another example, encapsulation of Type II oral poliovirus (OPV) in a single layer of EPO, a single layer of Glycol Chitosan, or a single layer of 50:50 mixture of EPO and glycol chitosan was achieved (FIG. 9). FIG. 9 shows the survival of OPV after 4 days at 37° C. with a normalizing control of identical Type II OPV from a fresh stock. $MgCl_2.6H_2O$ was used as a comparison with standard salt buffer.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A formulation of mucoadhesive polymeric encapsulated microorganisms thereof comprising a) single-cell microorganisms selected from the group consisting of yeast, bacteria, and viral particles in an effective amount to elicit an immune response to the microorganism, b) wherein each polymeric encapsulated microorganism has three alternating bilayers formed of a layer of an enteric pH responsive polymethacrylate polymer and a layer of a mucoadhesive polymer, wherein the polymethacrylate polymer is on the surface of the microrganisms and the mucoadhesive polymer is on the outer surface of the encapsulated microorganisms and can bind to mucosal surfaces of the gastrointestinal tract of a host, and wherein the polymethacrylate polymer is stable at an acidic pH and degrades at physiological pH so that the microorganisms are released from the polymer bilayers upon reaching the small intestine.

2. The formulation of claim 1, comprising one or more mucoadhesive polymers selected from the group consisting of chitosan, alginate, agarose, gelatin, hyaluronic acid, xanthan gum, guar gum, pectin, cellulose, and cellulose derivatives.

3. The formulation of claim 1, wherein the one or more mucoadhesive polymers are chitosan or alginate.

4. The formulation of claim 1, comprising one or more mucoadhesive polymers selected from the group consisting of polyacrylic acids, poly(methacryl acids), polymethacrylates, hydroxypropyl-methylcellulosephthalate (HPMC), hydrazine, acetal, ortho-ester-, and vinyl-ester functionalized polymers.

5. The formulation of claim 1, wherein the polymethacrylate polymer degrades at a pH within a range selected from the group consisting of from about 6.1 to about 7.4 inclusive, from about 6.8 to about 7.9 inclusive, from about 5.2 to about 6.7 inclusive, and from about 5.2 to about 7.0 inclusive.

6. The formulation of claim 5, wherein the microorganism is a probiotic microorganism.

7. The formulation of claim 6, wherein the microorganism is selected from the group consisting of *Bacillus coagulans, Lactobacillus acidophilus, Bifidobacterium longum, Bifidobacterium bifidum, Lactobacillus fermentum, Lactobacillus rhamnosus, Streptococcus thermophiles, Bifidobacterium breve, Lactobacillus reuteri, Saccharomyces boulardii*, and any genetically-modified variants thereof.

8. The formulation of claim 7, wherein the probiotic bacteria are genetically engineered to express one or more recombinant proteins.

9. The formulation of claim 8, wherein the recombinant proteins are selected from the group consisting of diagnostic, prophylactic, and therapeutic proteins.

10. The formulation of claim 1, wherein the microorganism is a live attenuated vaccine.

11. The formulation of claim 1, wherein the microorganism is lyophilized.

12. The formulation of claim 1, wherein the microorganism is administered in a dosage unit for replacement of the microorganism in the gastrointestinal tract.

13. The formulation of claim 1 is formulated in a pharmaceutical composition for enteral administration.

14. The formulation of claim 1 further comprising therapeutic, prophylactic or diagnostic agents.

15. A method for the treatment or prevention of one or more diseases or conditions associated with an alteration in the gut microbiota, comprising administering to the subject an effective amount of a formulation of claim 1.

16. The method of claim 15, wherein the one or more diseases or conditions are selected from the group consisting of Crohn's disease, ulcerative colitis, gluten insensitivity, lactose intolerance, obesity, asthma, allergies, metabolic syndrome, diabetes, psoriasis, eczema, rosacea, atopic dermatitis, gastrointestinal reflux disease, cancers of the gastrointestinal tract, bacterial vaginosis, neurodevelopmental conditions, and general lowered immunity following a course of antibiotics or chemotherapy.

17. The method of claim 15 comprising repeating the administration of the formulation for a time and in an amount effective to alleviate one or more symptoms of a disease or condition.

* * * * *

UNITED STATES PATENT AND TRADEMARK OFFICE
CERTIFICATE OF CORRECTION

PATENT NO. : 10,548,844 B2
APPLICATION NO. : 15/372703
DATED : February 4, 2020
INVENTOR(S) : Aaron C. Anselmo, Robert S. Langer and Ana Jaklenec It is certified that error appears in the above-identified patent and that said Letters Patent is hereby corrected as shown below:

In the Claims

Claim 4, Column 38, Line 23, replace "poly(methacryl acids)" with --poly(methacrylic acids)--.
Claim 13, Column 38, Line 55, replace "claim 1 is formulated" with --claim 1 formulated--.

Signed and Sealed this
Twelfth Day of January, 2021

Andrei Iancu
*Director of the United States Patent and Trademark Office*